United States Patent [19]

Capon et al.

[11] Patent Number: 5,359,046
[45] Date of Patent: Oct. 25, 1994

[54] CHIMERIC CHAINS FOR RECEPTOR-ASSOCIATED SIGNAL TRANSDUCTION PATHWAYS

[75] Inventors: Daniel J. Capon, Hillsborough; Arthur Weiss, Mill Valley; Brian A. Irving; Margo R. Roberts, both of San Francisco; Krisztina Zsebo, Woodside, all of Calif.

[73] Assignees: Cell Genesys, Inc., Foster City; The Regents of the University of California, Oakland, both of Calif.

[21] Appl. No.: 988,194

[22] Filed: Dec. 9, 1992

Related U.S. Application Data

[63] Continuation-in-part of Ser. No. 627,643, Dec. 14, 1990, abandoned.

[51] Int. Cl.$^5$ ............ C07H 17/00; A61K 35/14; C12P 21/00; C07K 3/00
[52] U.S. Cl. .................... 536/23.4; 435/6; 435/69.1; 435/240.2; 435/240.1; 435/320.1; 435/235; 536/23.1; 536/23.5; 536/23.51; 536/23.52; 536/23.53; 530/350; 530/387.1; 530/387.3; 530/387.7; 530/387.9; 530/388.1
[58] Field of Search ............ 435/6, 69.1, 69.5, 69.7, 435/240.2, 240.1, 320.2, 235, 7, 70.21, 70.2; 536/23.1-23.53; 530/350, 351, 387, 388; 424/85.1-85.8, 93; 514/2, 8, 12

[56] References Cited

U.S. PATENT DOCUMENTS 4,946,778 8/1990 Ladner et al. .
5,091,513 2/1992 Huston et al. .

FOREIGN PATENT DOCUMENTS 0314317 5/1989 European Pat. Off. .
0340793 11/1989 European Pat. Off. .
WO90/04640 5/1990 WIPO .
WO91/10736 7/1991 WIPO .
WO92/15322 9/1992 WIPO .
WO93/19163 9/1993 WIPO .

OTHER PUBLICATIONS

Weissman et al. (Dec., 1988) PNAS, vol. 85: pp. 9709–9713.
Lanier et al. (14 Dec. 1989) Nature, vol. 342: pp. 803–805.
Byrn et al. (12 Apr. 1990) Nature, vol. 344; pp. 667–670.
Orloff et al. (13 Sep. 1990) Nature, vol. 347:189–191.
Littman et al. (Feb. 1985) Cell, vol. 40:pp. 237–246.
Kinet (May 5, 1989) Cell, vol. 57, pp. 351–354.
Kuwana, et al. (1987) Biochemical and Biophysical Research Communication 149(3):960–968.
Reidel et al. (1986) Nature 324:68–70.
Reidel, et al. (1989) EMBO J. 8(10):2943–2954.
Whitlow, et al. (1991) Meth. In Enzymol. 2:97–105.
Kolanus, et al. (1993) Cell 74:171–183.
Ra, et al. (1989) J. Biol. Chem. 264:15323–15327.

(List continued on next page.)

Primary Examiner—Robert J. Hill, Jr.
Assistant Examiner—Gian P. Wang
Attorney, Agent, or Firm—Bertram I. Rowland

[57] ABSTRACT

Chimeric proteins and DNA sequence encoding chimeric proteins are provided, where the chimeric proteins are characterized by an extracellular domain capable of binding to a ligand in a non-MHC restricted manner, a transmembrane domain and a cytoplasmic domain capable of activating a signaling pathway. The extracellular domain and cytoplasmic domain are not naturally found together. Binding of ligand to the extracellular domain results in transduction of a signal and activation of a signaling pathway in the cell, whereby the cell may be induced to carry out various functions relating to the signalling pathway. A wide variety of extracellular domains may be employed as receptors, where such domains may be naturally occurring or synthetic. The chimeric DNA sequences may be used to modify lymphocytes as well as hematopoietic stem cells as precursors to a number of important cell types.

21 Claims, 10 Drawing Sheets

OTHER PUBLICATIONS

Irving, et al., The Cytoplasmic Domain of the T Cell Receptor ξ Chain is Sufficient to Couple to Receptor-Associated Signal Transduction Pathways, *Cell* 64, 891–901 (1991).

Romeo, et al., Cellular Immunity to HIV Activated by CD4 Fused to T Cell or Fc Receptor Polypeptides, *Cell* 64, 1037–1046 (1991).

Letourneur, et al., T-cell and basophil activation through the cytoplasmic tail of T-cell-receptor ξ family proteins, *Proc. Natl. Acad. Sci. USA* 88, 8905–8909 (1991).

Romeo, et al., *Sequence Requirements for Induction of Cytolysis by the T Cell Antigen/Fc Receptor ξ Chain*, Cell 68, 889–897 (1992).

Goldsmith, et al., Isolation and characterization of a T-lymphocyte somatic mutant with altered signal transduction by the antigen receptor, *Proc. Natl. Acad. Sci. USA* 84, 6879–6883 (1987).

Letourneur, et al., Activation of T Cells by a Tyrosine Kinase Activation Domain in the Cytoplasmic Tail of CD3 ε, *Science,* 79–81 (1992).

Chan, et al., The ξ chain is associated with a tyrosine kinase and upon T-cell antigen receptor stimulation associates with ZAP-70, a 70-kDa tyrosine phosphoprotein, *Proc. Natl. Acad. Sci. USA* 88, 9166–9170 (1991).

Gross, et al., Expression of immunoglobulin-T-cell receptor chimeric molecules as functional receptors with antibody-type specificity, *Proc. Natl. Acad. Sci. USA* 86, 10024–10028 (1989).

Becker, et al., *Expression of a Hybrid Immunoglobulin-T Cell Receptor Protein in Transgenic Mice*, Cell 58, 911–921 (1989).

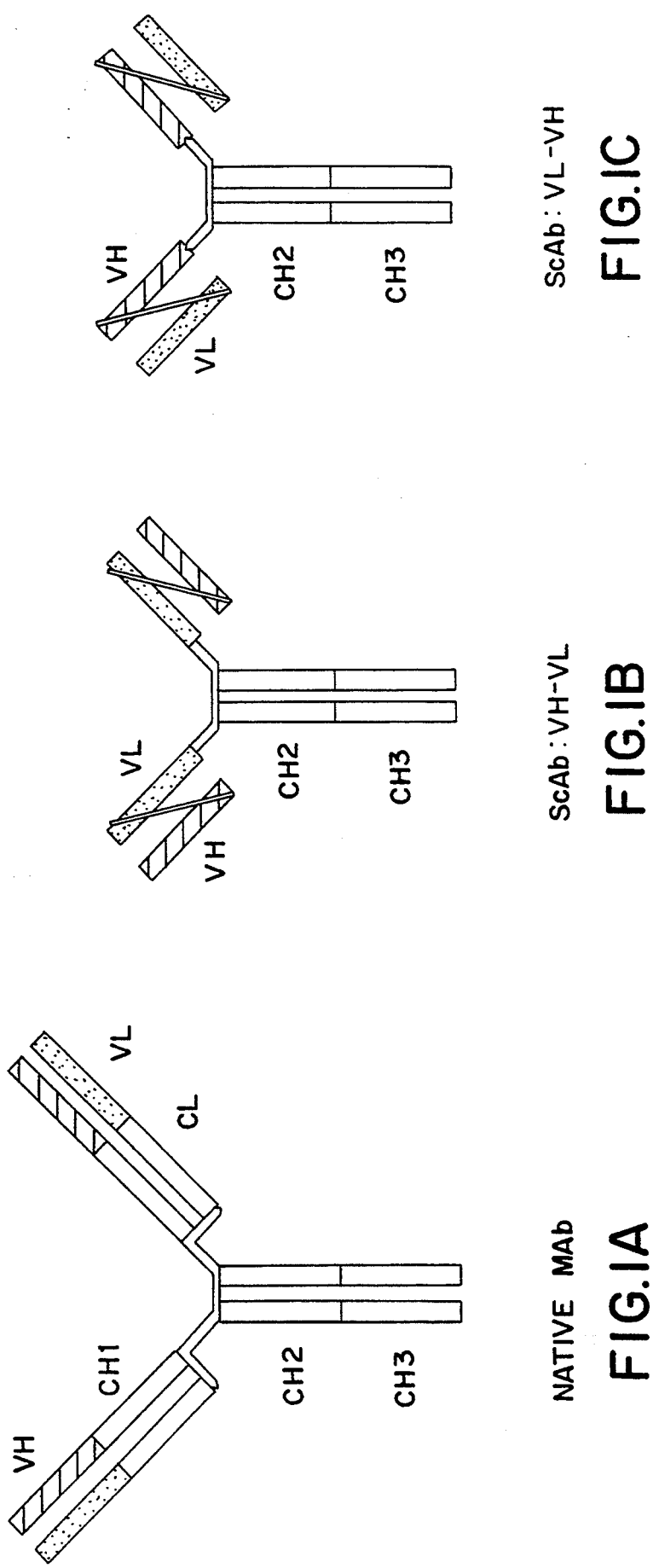

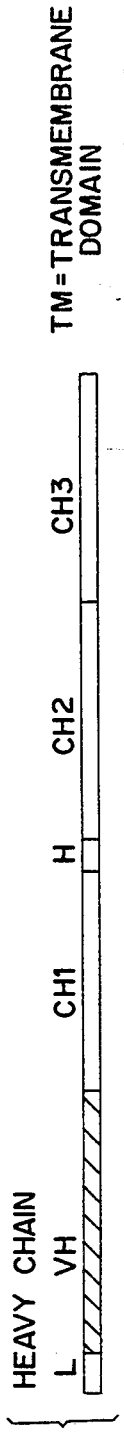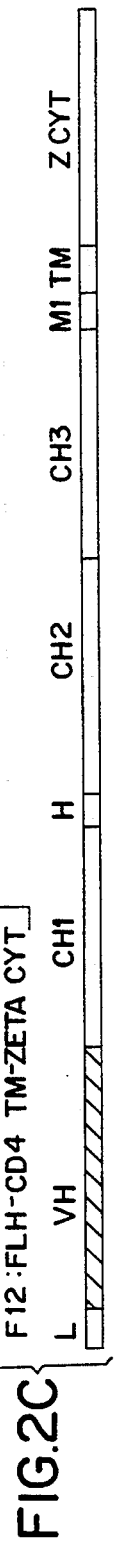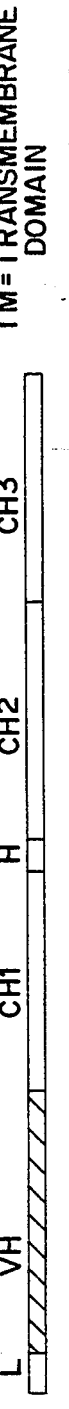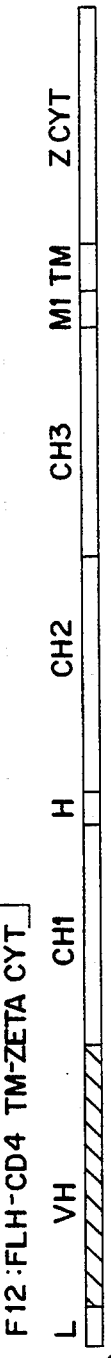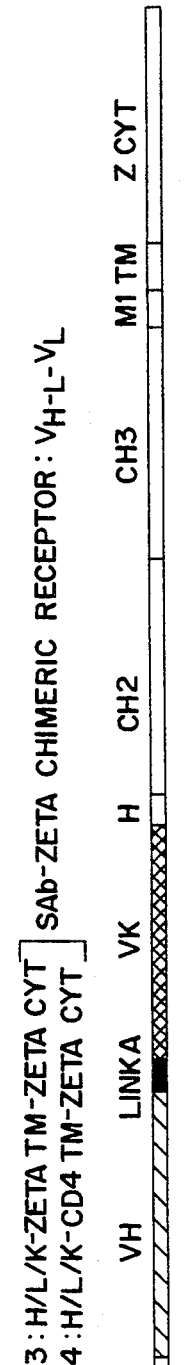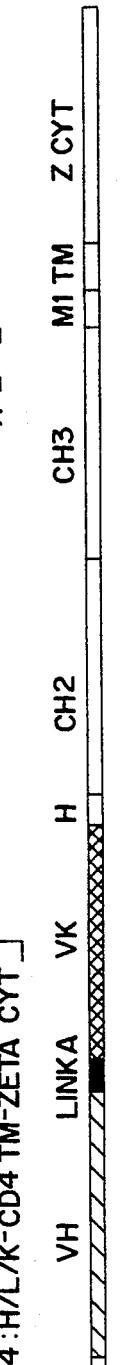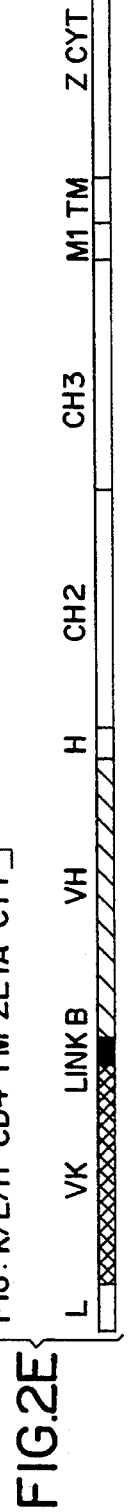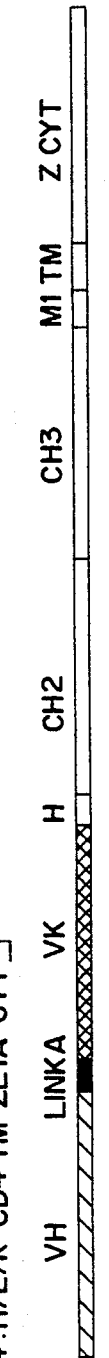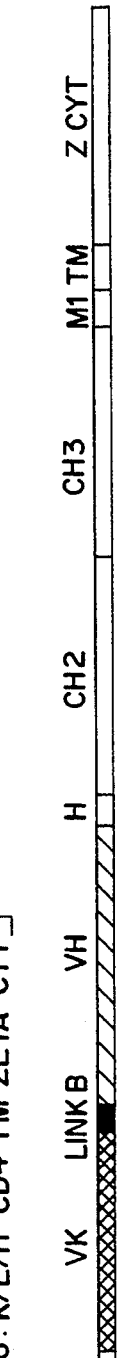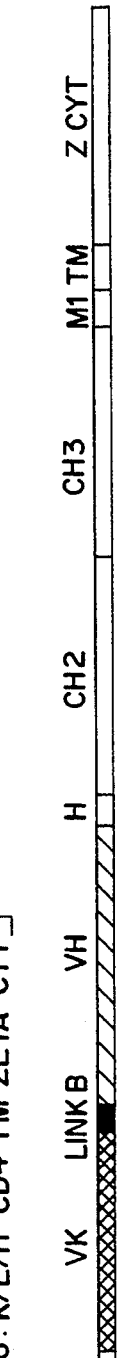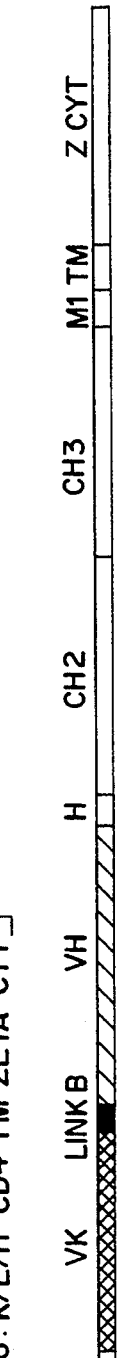

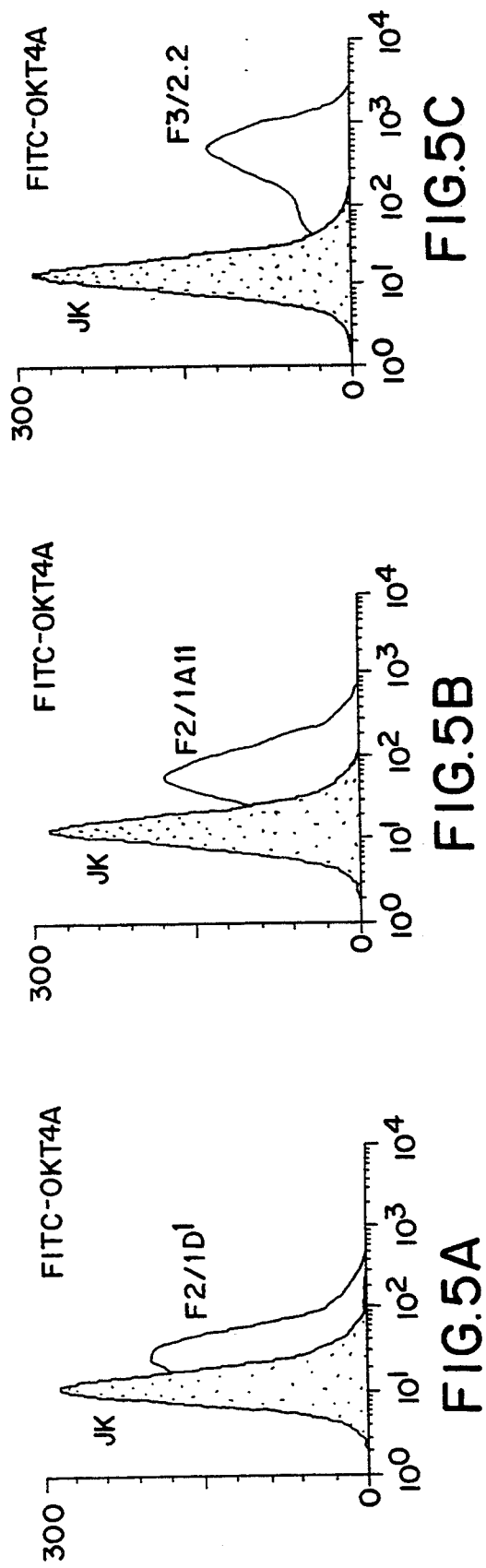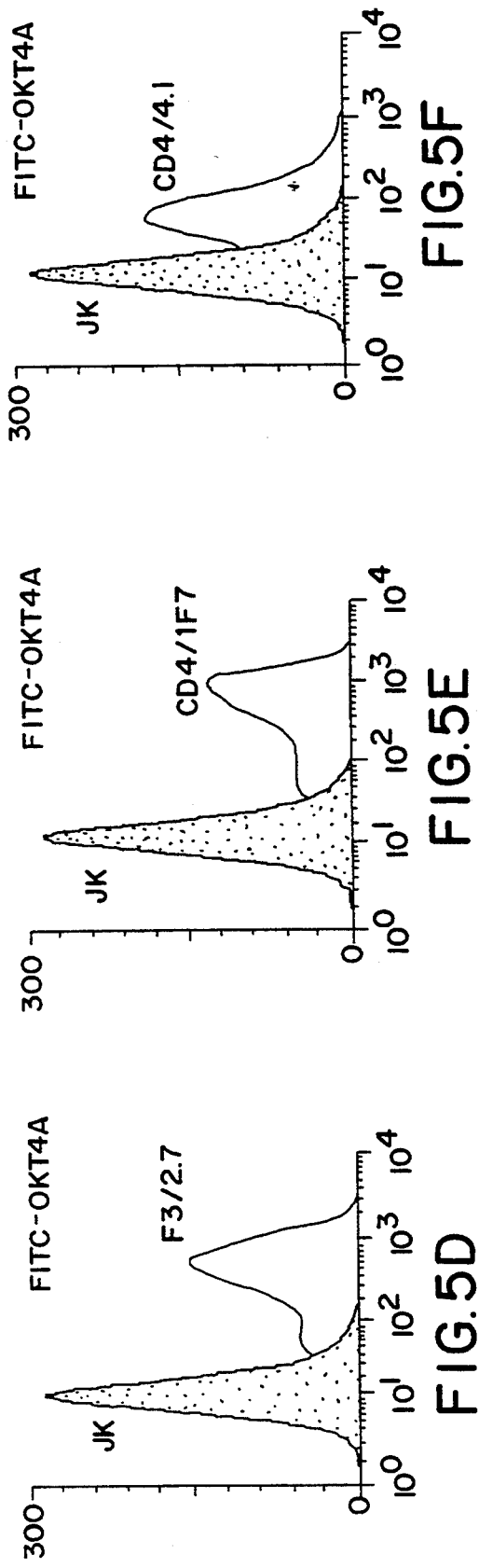

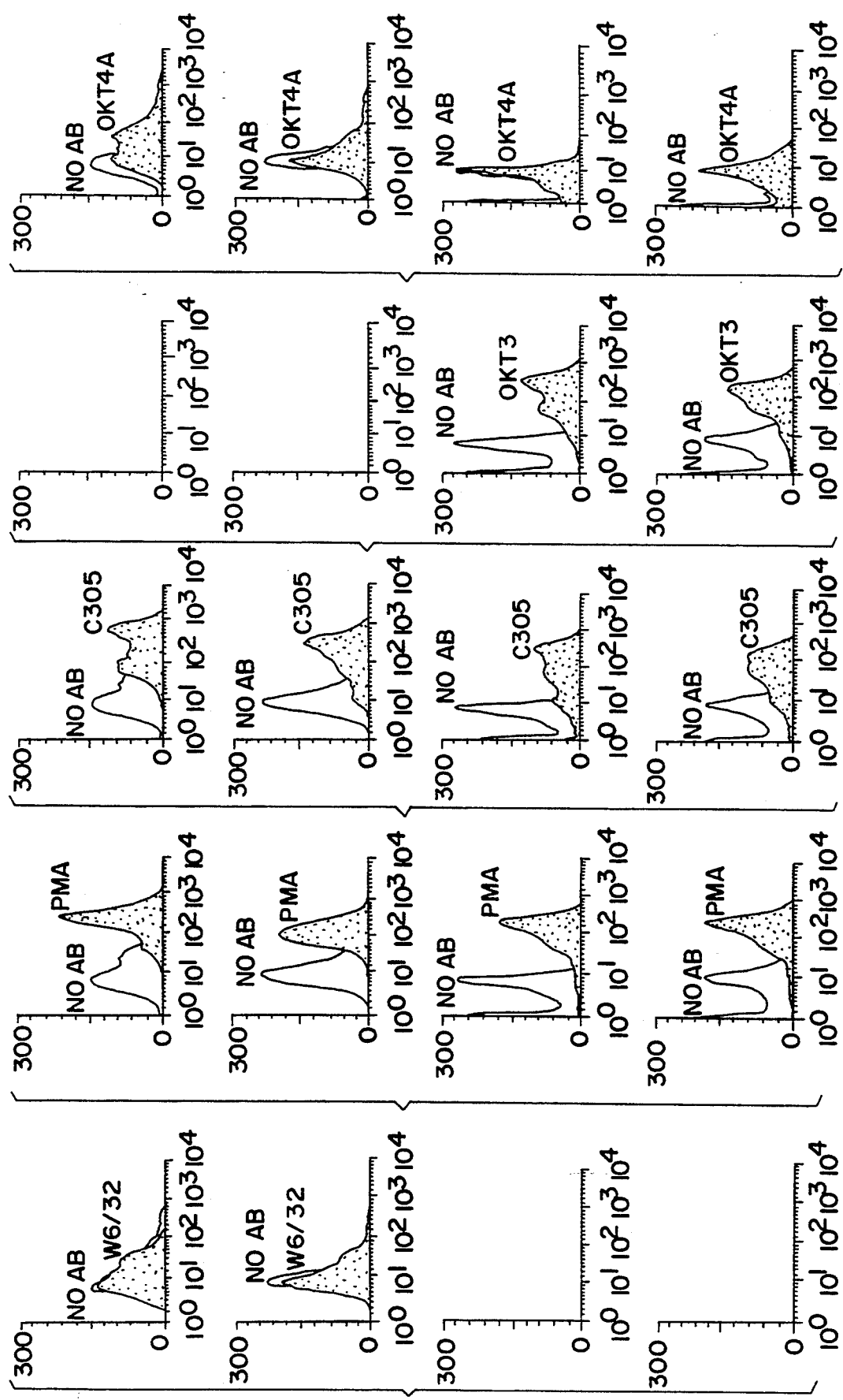

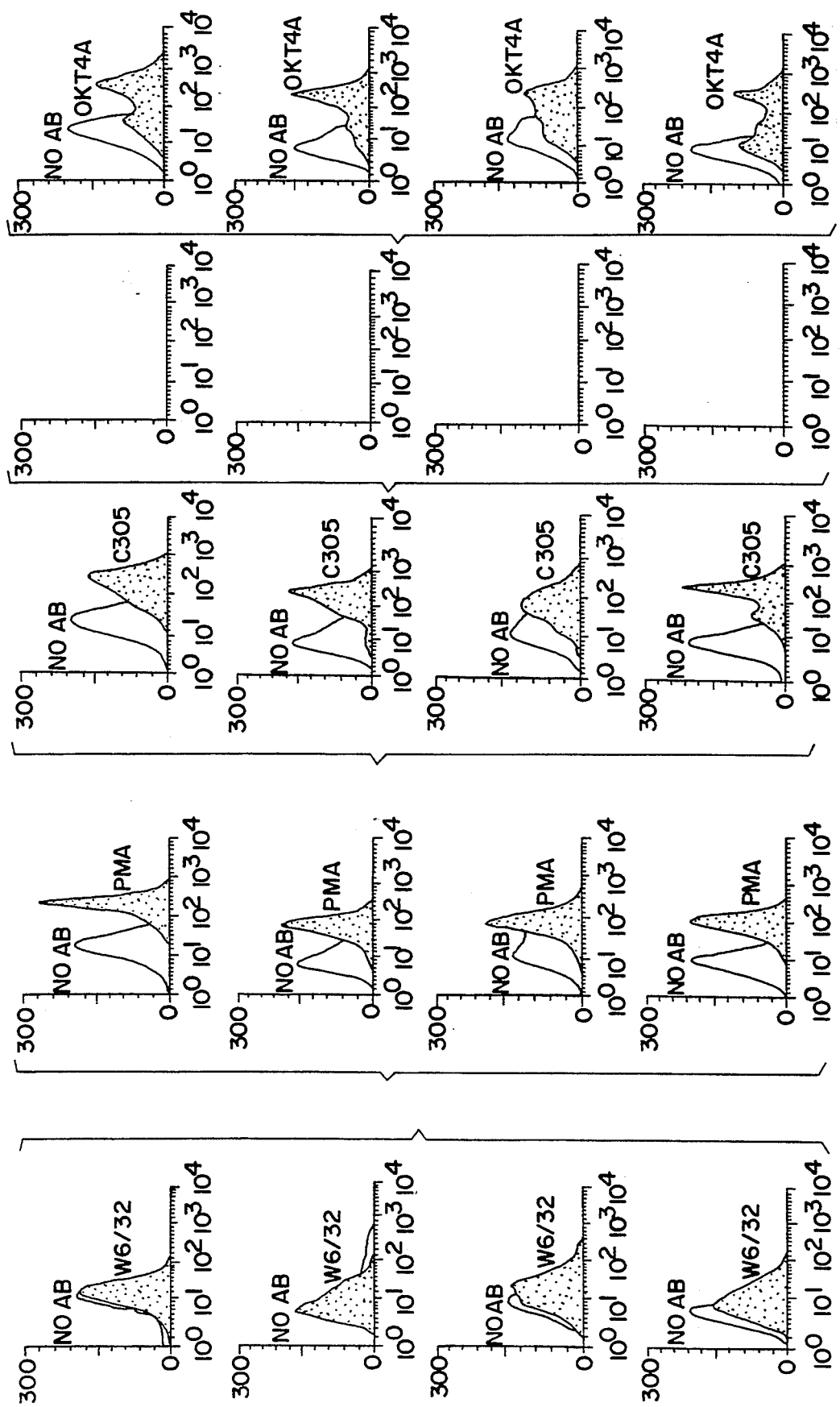

Oligonucleotides

1. GGAATTCGCTAGCTTTCCAGGACAAAACTCACACATGC
2. CGGAGATCTCGTGCGACCGCGAGAGCC
3. GGAATTCGCTAGCTTTCCAGGAGCGCAAATGTTGTGTC
4. CGGAGATCTC(A/G)CGCGACCCCGAGAGCC
5. CAGGTAGCAGAGTTTGGGAGACAGGGAGAGGCTCTT
6. AGTTTGGGAGACAGGG
7. CGGGATCCAGAGCTGCAACTGGAG
8. GAAGATCTGACCTTGAAGAAGGTGAC
9. TCTCCTCCAGTTGCAGCTCCGGAGACAGGGAGAGGC
10. TTGCAGCTCCGGAGAC
11. ATCCAGCAGGTAGCAGAGGTCCAGCTCCCCGTCCTG
12. TAGCAGAGGTCCAGCT
13. CCTGCTGAACTTCACTCTGAAGAAGGTGACGGTGGC
14. TTCACTCTGAAGAAGG
15. CAGCACAATCAGGGCCATGTCCAGCTCCCCGTCCTG
16. AGGGCCATGTCCAGCT
17. CGGAATTCGGTACCTCCTGTGCAAGAAC
18. CGGAATTCGCCTCCACCAAGGGCCCA
19. CGGAATTCACGCGTCCCAGTCAGGACACAGC
20. GAGAGAGATCTGCTAGCGGTCAGGCTGGAACTGAG
21. GCATGTGTGAGTTTTGTCTGAGGAGACGGTGACCAG
22. GTTTTGTCTGAGGAGA
23. GTGACAGTCGACCCCTTGAAGTCCACTTTGGT
24. CCACCCCTCACTCTGCTTCTC
25. TCGACCAGCGGCAGCGGCAAGAGCAGCGAGGGTAAGGGTACCA
26. GATCTGGTACCCTTACCCTCGCTGCTCTTGCCGCTGCCGCTGG
27. CTCCTGTAGTAGCACCTGACCCTTACCCTCGCTGCT
28. AGCACCTGACCCTTAC
29. GCATGTGTGAGTTTTGTCCTTGAAGTCCACTTTGGT
30. GTTTTGTCCTTGAAGT
31. GTGACACTCGAGACGGTGACCAGGAGT
32. TCGAGCGGCGGTGGAGGTAGCGGAGGTGGCGGATCTGGAGGCGGTGGTAGCACGCGTA
33. GATCTACGCGTGCTACCACCGCCTCCAGATCCGCCACCTCCGCTACCTCCACCGCCGC
34. CTGGGTCAACTGGATGTCGCTACCACCGCCTCCAGA

FIG.10

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

GGAATTCGCT AGCTTTCCAG GACAAAACTC ACACATGC            38

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

CGGAGATCTC GTGCGACCGC GAGAGCC            27

( 2 ) INFORMATION FOR SEQ ID NO:3:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

GGAATTCGCT AGCTTTCCAG GAGCGCAAAT GTTGTGTC            38

( 2 ) INFORMATION FOR SEQ ID NO:4:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:4:

CGGAGATCTC RCGCGACCCC GAGAGCC 27

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CAGGTAGCAG AGTTTGGGAG ACAGGGAGAG AGCTCTT 37

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AGTTTGGGAG ACAGGG 16

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGGGATCCAG AGCTGCAACT GGAG 24

( 2 ) INFORMATION FOR SEQ ID NO:8:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GAAGATCTGA CCTTGAAGAA GGTGAC 26

( 2 ) INFORMATION FOR SEQ ID NO:9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TCTCCTCCAG TTGCAGCTCC GGAGACAGGG AGAGGC 36

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TTGCAGCTCC GGAGAC                      16

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ATCCAGCAGG TAGCAGAGGT CCAGCTCCCC GTCCTG         36

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

TAGCAGAGGT CCAGCT                      16

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CCTGCTGAAC TTCACTCTGA AGAAGGTGAC GGTGGC         36

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TTCACTCTGA AGAAGG                      16

( 2 ) INFORMATION FOR SEQ ID NO:15:

( i ) SEQUENCE CHARACTERISTICS:
        ( A ) LENGTH: 36 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:15:

CAGCACAATC AGGGCCATGT CCAGCTCCCC GTCCTG 36

( 2 ) INFORMATION FOR SEQ ID NO:16:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AGGGCCATGT CCAGCT 16

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CGGAATTCGG TACCTCCTGT GCAAGAAC 28

( 2 ) INFORMATION FOR SEQ ID NO:18:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CGGAATTCGC CTCCACCAAG GGCCCA 26

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

CGGAATTCAC GCGTCCCAGT CAGGACACAG C 31

( 2 ) INFORMATION FOR SEQ ID NO:20:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

GAGAGAGATC TGCTAGCGGT CAGGCTGGAA CTGAG 35

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GCATGTGTGA GTTTTGTCTG AGGAGACGGT GACCAG                                      36

( 2 ) INFORMATION FOR SEQ ID NO:22:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GTTTTGTCTG AGGAGA                                                              16

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GTGACAGTCG ACCCCTTGAA GTCCACTTTG GT                                         32

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

CCACCCCTCA CTCTGCTTCT C                                                      21

( 2 ) INFORMATION FOR SEQ ID NO:25:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

TCGACCAGCG GCAGCGGCAA GAGCAGCGAG GGTAAGGGTA CCA                           43

( 2 ) INFORMATION FOR SEQ ID NO:26:

( i ) SEQUENCE CHARACTERISTICS:
        ( A ) LENGTH: 43 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:26:

GATGTGGTAC CCTTACCCTC GCTGCTCTTG CCGCTGCCGC TGG  43

( 2 ) INFORMATION FOR SEQ ID NO:27:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:27:

CTCCTGTAGT AGCACCTGAC CCTTACCCTC GCTGCT  36

( 2 ) INFORMATION FOR SEQ ID NO:28:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:28:

AGCACCTGAC CCTTAC  16

( 2 ) INFORMATION FOR SEQ ID NO:29:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:29:

GCATGTGTGA GTTTTGTCCT TGAAGTCCAC TTTGGT  36

( 2 ) INFORMATION FOR SEQ ID NO:30:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:30:

GTTTTGTCCT TGAAGT  16

( 2 ) INFORMATION FOR SEQ ID NO:31:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:31:

GTGACACTCG AGACGGTGAC CAGGAGT                                                27

( 2 ) INFORMATION FOR SEQ ID NO:32:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

TCGAGCGGCG GTGGAGGTAG CGGAGGTGGC GGATCTGGAG GCGGTGGTAG CACGCGTA         58

( 2 ) INFORMATION FOR SEQ ID NO:33:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

GATCTACGCG TGCTACCACC GCCTCCAGAT CCGCCACCTC CGCTACCTCC ACCGCCGC         58

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

CTGGGTCAAC TGGATGTCGC TACCACCGCC TCCAGA                                 36

( 2 ) INFORMATION FOR SEQ ID NO:35:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

GGTCGACCTG GATCCGCCAT ACCACATTTG TAG                                    33

( 2 ) INFORMATION FOR SEQ ID NO:36:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

GCCGCGGCTC TAGAGCCAGA CATGATAAGA TAC                                    33

( 2 ) INFORMATION FOR SEQ ID NO:37:

( i ) SEQUENCE CHARACTERISTICS:
        ( A ) LENGTH: 33 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:37:

AAGCTTGTGC TAGCTATCCC GCCCCTAACT CCG    33

( 2 ) INFORMATION FOR SEQ ID NO:38:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:38:

CGAATTCGGT CGACCGCAAA AGCCTAGGCC TCC    33

( 2 ) INFORMATION FOR SEQ ID NO:39:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:39:

GTCTATAGCA TGCTCCCCTG CTCCGACCCG    30

( 2 ) INFORMATION FOR SEQ ID NO:40:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:40:

GGTACCGAAT TCTCCTGCGG GGAGAAGCAG    30

( 2 ) INFORMATION FOR SEQ ID NO:41:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:41:

CGCCAAGCTT GGCCATTGCA TACGGT    26

( 2 ) INFORMATION FOR SEQ ID NO:42:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:42:

GAGGTCTAGA CGGTTCACTA AACGAGCTCT　　　　　　　　　　　　　　　　　　　　　　　30

( 2 ) INFORMATION FOR SEQ ID NO:43:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

Gly Gly Gly Gly Ser Gly Gly Gly Gly Ser Gly Gly Gly Gly Ser
1           5               10             15

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:44:

GATCATGGCG CCAGAACTGC ATGGAGATGG　　　　　　　　　　　　　　　　　　　　　　　30

( 2 ) INFORMATION FOR SEQ ID NO:45:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:45:

GATCATGGGC CCAGTGTTCT CCAGAGGGTC　　　　　　　　　　　　　　　　　　　　　　　30

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:46:

GATCATGGCG CCCAGAGCTG TGTGGAGCTG　　　　　　　　　　　　　　　　　　　　　　　30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:47:

GATCATGGGC CCGCCACCAG GTGCAGGTTC　　　　　　　　　　　　　　　　　　　　　　　30

( 2 ) INFORMATION FOR SEQ ID NO:48:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:48:

GATCATGGCG CCCAGAACTG CATTGAACTA     30

(2) INFORMATION FOR SEQ ID NO:49:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:49:

GATCATGGGC CCACTCTGAG TCCTGAGTTC     30

CHIMERIC CHAINS FOR RECEPTOR-ASSOCIATED SIGNAL TRANSDUCTION PATHWAYS

CROSS-REFERENCE TO GOVERNMENT GRANT

This application was made with grant number NIGMS 39553 awarded by the National Institutes of Health. The government may have certain rights in this invention.

CROSS-REFERENCE TO RELATED APPLICATIONS

This application is a continuation-in-part of application Ser. No. 07/627 643, filed Dec. 14, 1990, now abandoned, the entirety of which is included herein by reference.

INTRODUCTION

1. Technical Field

The field of this invention is the use of chimeric surface membrane proteins for signal transduction.

2. Background Art

Regulation of cell activities is frequently achieved by the binding of the ligand to a surface membrane receptor. The formation of the complex with the extracellular portion of the receptor results in a change in conformation with the cytoplasmic portion of the receptor undergoing a change which results in a signal being transduced in the cell. In some instances, the change in the cytoplasmic portion results in binding to other proteins, where the other proteins are activated and may carry out various functions. In some situations, the cytoplasmic portion is autophosphorylated or phosphorylated, resulting in a change in its activity. These events are frequently coupled with secondary messengers, such as calcium, cyclic adenosine monophosphate, inositol phosphate, diacylglycerol, and the like. The binding of the ligand results in a particular signal being induced.

There are a number of instances, where one might wish to have a signal induced by virtue of employing a different ligand. For example, one might wish to activate particular T-cells, where the T-cells will then be effective as cytotoxic agents, or activating agents by secretion of interleukins, colony stimulating factors or other cytokines, which results in the stimulation of another cell. The ability of the T-cell receptor to recognize antigen is restricted by the nature of Major Histocompatibility Complex (MHC) antigens on the surface of the host cell. Thus, the use of a chimeric T-cell receptor in which a non-MHC restricted ligand binding domain is linked directly to the signal transducing domain of the T-cell receptor would permit the use of the resulting engineered effector T-cell in any individual, regardless of their MHC genetic background. In this manner, one may change the ligand which initiates the desired response, where for some reason, the natural agent may not be as useful.

There is, therefore, interest in finding ways to modulate cellular responses in providing for the use of ligands other than the normal ligand to transduce a desired signal.

Relevant Literature

The T-cell antigen receptor (TCR) has a non-covalent association between a heterodimer, the antigen/MHC binding subunit Ti variable component and the five invariant chains: zeta ($\zeta$), eta ($\eta$) and the three CD3 chains: gamma ($\gamma$), delta ($\delta$) and epsilon ($\epsilon$) (Weiss and Imboden (1987) *Adv. Immunol.*, 41:1–38; Cleavers et al. (1988) *Ann. Rev. Immunol.*, 6:629–662; Frank et al. (1990) *Sem. Immunol.*, 2:89–97). In contrast to the Ti alpha/beta heterodimer which is solely responsible for antigen binding, the physically associated CD3-zeta/eta complex does not bind ligand, but is thought to undergo structural alterations as a consequence of Ti-antigen interaction which results in activation of intracellular signal transduction mechanisms.

A description of the zeta chain may be found in Ashwell and Klausner (1990) *Ann. Rev. Immunol.*, 8:139–167. The nature of the zeta chain in the TCR complex is described by Baniyash et al. (1988) *J. Biol. Chem.*, 263:9874–9878 and Orloff et al. (1989) ibid., 264:14812–14817. The heterodimeric zeta and eta protein is described by Jin et al. (1990) *Proc. Natl. Acad. Sci. USA*, 87:3319–3323. Discussion of the homo- and heterodimers may be found in Mercep et al. (1988) *Science*, 242:571–574; and Mercep et al. (1989) ibid., 246:1162–1165. See also Sussman et al. (1988) *Cell*, 52:85–95. For studies of the role of the zeta protein, see Weissman et al. (1989) *EMBO, J.*, 8:3651–3656; Frank et al. (1990) *Science*, 249:174–177; and Lanier et al. (1989) *Nature*, 342:803–805.

For discussion of the gamma subunit of the $Fc_\epsilon$ R1 receptor, expressed on mast cells and basophils and its homology to the zeta chain, see Bevan and Cunha-Melo (1988) *Prog. Allergy*, 42:123–184; Kinet (1989) *Cell*, 57:351–354; Benhamou et al., *Proc. Natl. Acad. Sci. USA*, 87:5327–5330; and Orloff et al. (1990) *Nature*, 347:189–191.

The zeta($\zeta$) chain is structurally unrelated to the three CD3 chains, and exists primarily as a disulfide-linked homodimer, or as a heterodimer with an alternatively spliced product of the same gene, eta ($\eta$). The zeta chain is also expressed on natural killer cells as part of the Fc$\gamma$RIII receptor. The gamma chain of the Fc$\epsilon$ receptor is closely related to zeta, and is associated with the Fc$\epsilon$RI receptor of mast cells and basophils and the C16 receptor expressed by macrophages and natural killer cells. The role in signal transduction played by the cytoplasmic domains of the zeta and eta chains, and the gamma subunit of the FcRI receptor has been described by Irving and Weiss (1991) *Cell* 64:891–901; Romeo and Seed, (1991) *Cell* 64:1037–1046 and Letourneur and Klausner (1991) *Proc. Natl. Acad. Sci. USA* 88:8905–8909. More recent studies have identified an 18 amino-acid motif in the zeta cytoplasmic domain that, upon addition to the cytoplasmic domain of unrelated transmembrane proteins, endows them with the capacity to initiate signal transduction (Romeo et al. (1992) *Cell* 68:889–897). These data suggest a T cell activation mechanism in which this region of zeta interacts with one or more intracellular proteins.

The three CD3 chains, gamma ($\gamma$), delta ($\delta$) and epsilon ($\epsilon$), are structurally related polypeptides and were originally implicated in signal transduction of T cells by studies in which anti-CD3 monoclonal antibodies were shown to mimic the function of antigen in activating T cells (Goldsmith and Weiss (1987) *Proc. Natl. Acad. Sci. USA* 84:6879–6883), and from experiments employing somatic cell mutants bearing defects in TCR-mediated signal transduction function (Sussman et al. (1988) *Cell* 52:85–95). Sequences similar to the active motif found in zeta are also present in the cytoplasmic domains of the CD3 chains gamma and delta. Chimeric receptors in which the cytoplasmic domain of an unrelated receptor has been replaced by that of CD3 epsilon have been shown to be proficient in signal transduction (Letourneur and Klausner (1992) *Science* 255:79-82), and a 22 amino acid sequence in the cytoplasmic tail of CD3 epsilon was identified as the sequence responsible. Although the cytoplasmic domains of both zeta and CD3 epsilon have been shown to be sufficient for signal transduction, quantitatively distinct patterns of tyrosine phosphorylation were observed with these two chains, suggesting that they may be involved in similar but distinct biochemical pathways in the cell.

The phosphatidylinositol-specific phospholipase C initiated activation by the T-cell receptor ("TCR") is described by Weiss et al. (1984) *Proc. Natl. Acad. Sci. USA*, 81:416-4173; and Imboden and Stobo (1985) *J. Exp. Med.*, 161:446-456. TCR also activates a tyrosine kinase (Samelson et al. (1986) *Cell*, 46:1083-1090; Patel et al. (1987) *J. Biol. Chem.*, 262:5831-5838; Chsi et al. (1989) *J. Biol. Chem* , 264:10836-10842, where the zeta chain is one of the substrates of the kinase pathway (Baniyash et al. (1988) *J. Biol. Chem.*, 263:18225-18230; Samelson et al. (1986), supra). Fyn, a member of the src family of tyrosine kinases, is reported to coprecipitate with the CD3 complex, making it an excellent candidate for a TCR-activated kinase (Samelson et al. (1990) *Proc. Natl. Acad. Sci. USA*, 87:4358-4362). In addition, a tyrosine kinase unrelated to fyn has been shown to interact with the cytoplasmic domain of zeta (Chan et al., (1991) *Proc. Natl. Acad. Sci. USA*, 88:9166-9170).

Letourner and Klausner (1991) *Proc. Natl. Acad. Sci. USA* 88:8905-8909 describe activation of T cells using a chimeric receptor consisting of the extracellular domains of the e chain of the human interleukin 2 receptor (Tac) and the cytoplasmic domain of either $\zeta$ or $\gamma$. Gross et al., (1989) *Proc. Natl. Acad. Sci. USA* 86: 10024-10028 describe activation of T cells using chimeric receptors in which the MHC-restricted antigen-binding domains of the T cell receptor $\alpha$ and $\beta$ chains were replaced by the antigen-binding domain of an antibody. Romeo and Seed (1991) *Cell* 64: 1037-1046 describe activation of T-cells via chimeric receptors in which the extracellular portion of CD4 is fused to the transmembrane and intracellular portions of $\gamma$, $\zeta$, and $\eta$ subunits. Letourner and Klausner (1992) describe activation of T cells by a chimeric receptor consisting of the extracellular domain of the IL-2 receptor and the cytoplasmic tail of CD3 epsilon (*Science* 255:79-82).

Based on the structural similarities between the immunoglobulin (Ig) chains of antibodies and the alpha ($\alpha$) and beta ($\beta$) T cell receptor chains (Ti), chimeric Ig-Ti molecules in which the V domains of the Ig heavy (VH) and light (VL) chains are combined with the C regions of Ti $\alpha$ and Ti $\beta$ chains have been described (Gross et al. (1989) *Proc. Natl. Acad. Sci. USA*, 86:1002-10028). The role of the Ti chains is to bind antigen presented in the context of MHC. The Ti heterodimer does not possess innate signalling capacity, but transmits the antigen-binding event to the CD3/zeta chains present in the TCR complex. Expression of a functional antigen-binding domain required co-introduction of both VH-Ti and VL-Ti chimeric molecules. These chimeras have been demonstrated to act as functional receptors by their ability to activate T cell effector function in response to cross-linking by the appropriate hapten or anti-idiotypic antibody (Becker et al. (1989) *Cell*, 58:911 and Gross et al. (1989) *Proc. Natl. Acad. Sci. USA* 86:10024). However, like the native Ti chains, the VH-Ti and VL-Ti chains do not possess innate signalling capacity, but act via the CD3/zeta complex.

SUMMARY OF THE INVENTION

The triggering of signal transduction leading to cytotoxic function by different cells of the immune system can be initiated by chimeric receptors with antibody type specificity. These chimeric receptors by-pass the requirement for matching at the MHC locus between target cell (i.e. virally infected, tumor cell, etc.) and effector cell (i.e., T cell, granulocyte, mast cell, etc.). Intracellular signal transduction or cellular activation is achieved by employing chimeric proteins having a cytoplasmic region associated with transduction of a signal and activation of a secondary messenger system, frequently involving a kinase, and a non-MHC restricted extracellular region capable of binding to a specific ligand and transmitting to the cytoplasmic region the formation of a binding complex. Particularly, cytoplasmic sequences of the zeta, eta, delta, gamma and epsilon chains of TCR and the gamma chain of Fc$_\epsilon$ R1 are employed joined to other than the natural extracellular region by a transmembrane domain. In this manner, cells capable of expressing the chimeric protein can be activated by contact with the ligand, as contrasted with the normal mode of activation for the cytoplasmic portion.

DESCRIPTION OF THE DRAWINGS

FIG. 1A, FIG. 1B and FIG. 1C are a diagrammatic depiction of the structure of single-chain antibodies used in the chimeric receptors of the invention as compared to the structure of native monoclonal antibodies.

FIG. 2A, FIG. 2B, FIG. 2C, FIG. 2D and FIG. 2E are a depiction of human anti-HiV gp41 monoclonal antibody 98.6 and single-chain antibody-zeta chimeric receptors of the invention.

FIG. 5A, FIG. 5B, FIG. 5C, FIG. 5E and FIG. 5F are graphs of FACS analysis of induction of CD69 expression after stimulation of native and chimeric receptors as described in Example 2, infra.

FIG. 7A, FIG. 7B, FIG. 7C, FIG. 7D and FIG. 7E are graphs of FACS analysis of CD69 expression in Jurkat cells expressing CD4, upon stimulation with various agents as described in Example 2, infra (FIG. 7A: treatment with W6/32 antibody as negative control; FIG. 7B: treatment with PMA; FIG. 7C: stimulation of native Ti with immobilized C305 mAb; FIG. 7D: stimulation of native CD3 with immobilized OKT3 mAb; FIG. 7E: stimulation of the V1 domain of CD4 by immobilized OKT4A).

FIG. 8A, FIG. 8B, FIG. 8C, FIG. 8D and FIG. 8E are graphs of FACS analysis of CD69 expression in Jurkat cells expressing the F2 chimeric receptor, upon stimulation with various agents as described in Example 2, infra (FIG. 8A: treatment with W6/32 antibody as negative control; FIG. 8B: treatment with PMA; FIG.

8C: stimulation of native Ti with immobilized C305 mAb; FIG. 8D: stimulation of native CD3 with immobilized OKT3 mAb; FIG. 8E: stimulation of the V1 domain of CD4 by immobilized OKT4A).

FIG. 9B: treatment with PMA; FIG. 9C: stimulation of native Ti with immobilized C305 mAb; FIG. 9D: stimulation of native CD3 with immobilized OKT3 mAb; FIG. 9E: stimulation of the V1 domain of CD4 by immobilized OKT4A).

FIG. 10 is a listing of oligonucleotides (SEQ ID NOS:01-34) as described in Example 3, infra.

DESCRIPTION OF THE SPECIFIC EMBODIMENTS

Figure 3A:
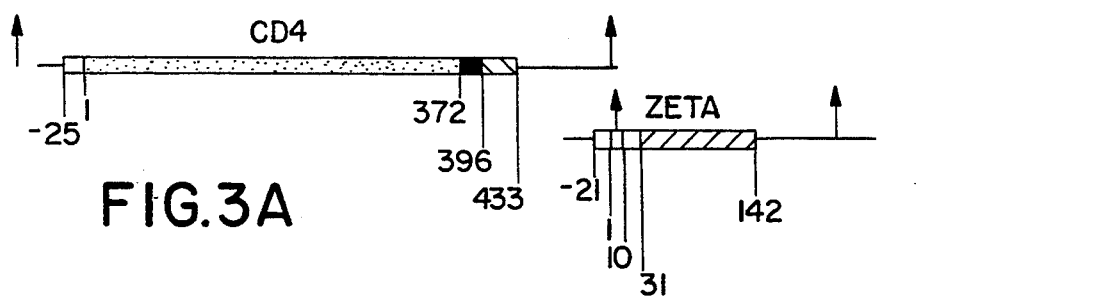
FIG. 3A, FIG. 3B, FIG. 3C, FIG. 3D and FIG. 3E are an illustration of the CD4-zeta chimeric receptors F1, F2 and F3 as described in Example 2, infra.
Figure 3B:
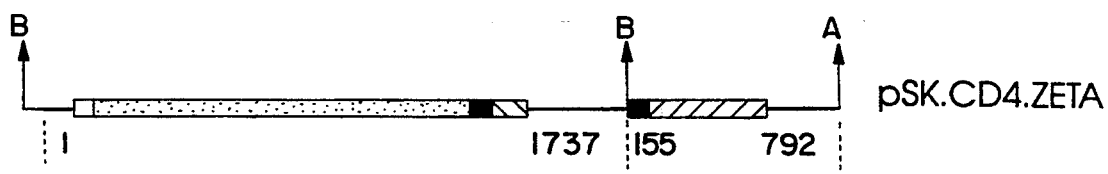
Figure 3C:
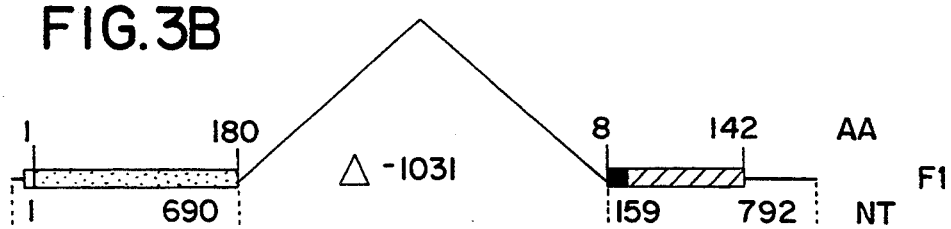
Figure 3D:
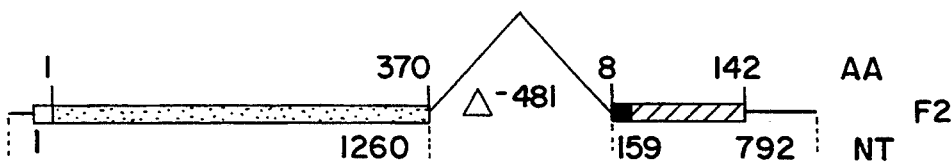
Figure 3E:
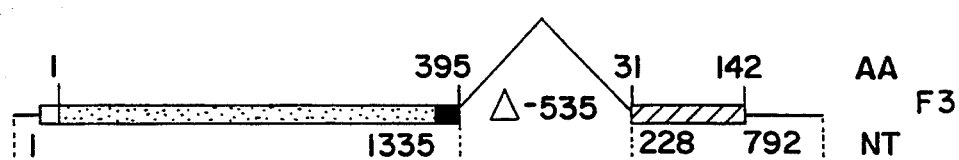
Figure 4A:
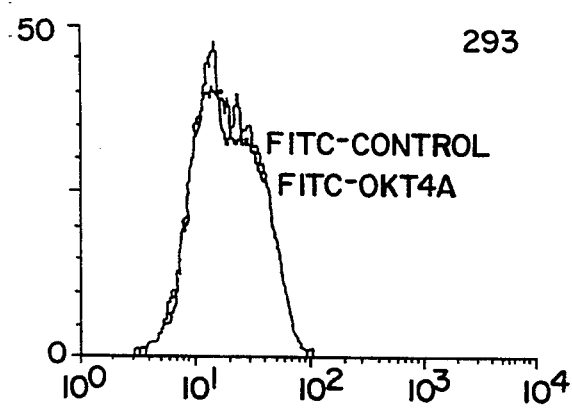
FIG. 4A, FIG. 4B, FIG. 4C, FIG. 4D and FIG. 4E are graphs of FACS analysis of expression of CD4-zeta chimeric receptors in the human cell line 293, as described in Example 2, infra.
Figure 4B:
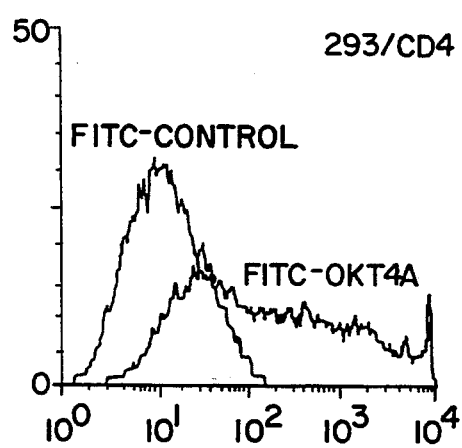
Figure 4C:
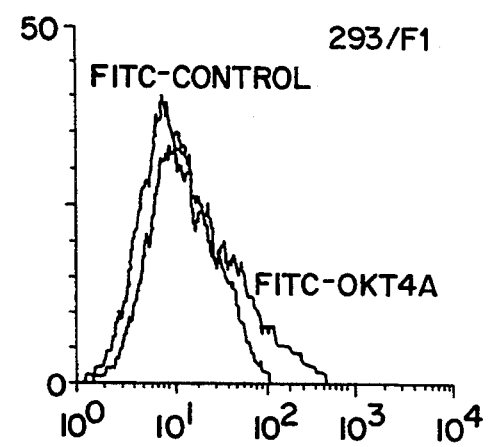
Figure 4D:
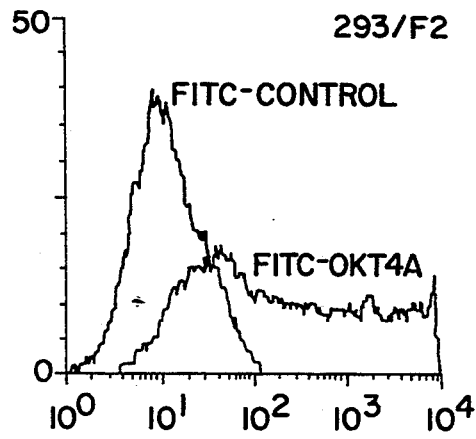
Figure 4E:
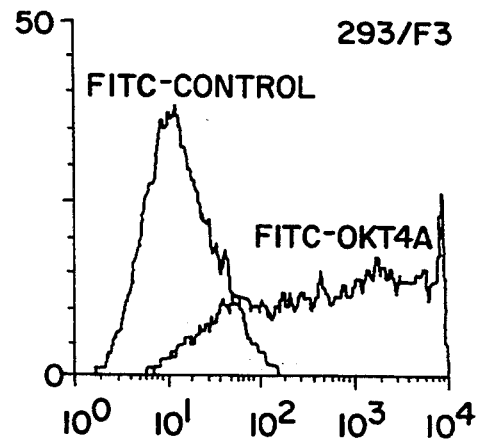

Novel DNA sequences, such DNA sequences as parts of expression cassettes and vectors, as well as their presence in cells are provided, where the novel sequences comprise three domains which do not naturally exist together: (1) a cytoplasmic domain, which normally transduces a signal resulting in activation of a messenger system, (2) a transmembrane domain, which crosses the outer cellular membrane, and (3) a non-MHC restricted extracellular receptor domain which serves to bind to a ligand and transmit a signal to the cytoplasmic domain, resulting in activation of the messenger system.

The cytoplasmic domain may be derived from a protein which is known to activate various messenger systems, normally excluding the G proteins. The protein from which the cytoplasmic domain is derived need not have ligand binding capability by itself, it being sufficient that such protein may associate with another protein providing such capability. Cytoplasmic regions of interest include the zeta chain of the T-cell receptor, the eta chain, which differs from the zeta chain only in its most C-terminal exon as a result of alternative splicing of the zeta mRNA, the delta, gamma and epsilon chains of the T-cell receptor (CD3 chains) and the gamma subunit of the $Fc_\epsilon R1$ receptor, and such other cytoplasmic regions which are capable of transmitting a signal as a result of interacting with other proteins capable of binding to a ligand.

A number of cytoplasmic regions or functional fragments or mutants thereof may be employed, generally ranging from about 50 to 500 amino acids, where the entire naturally occurring cytoplasmic region may be employed or only an active portion thereof. The cytoplasmic regions of particular interest are those which may be involved with one or more secondary messenger pathways, particular pathways involved with a protein kinase, more particularly, protein kinase C (PKC).

Pathways of interest include the phosphatidylinositol-specific phospholipase involved pathway, which is normally involved with hydrolysis of Phosphatidylinositol-4,5-bisphosphate, which results in production of the secondary messengers inositol-1,4,5-trisphosphate and diacylglycerol. Another pathway is the calcium mediated pathway, which may be as a result of direct or indirect activation by the cytoplasmic portion of the chimeric protein. Also, by itself or in combination with another pathway, the kinase pathway may be involved, which may involve phosphorylation of the cytoplasmic portion of the chimeric protein. One or more amino acid side chains, particularly tyrosines, may be phosphorylated. There is some evidence that fyn, a member of the src family of tyrosine kinases, may be involved with the zeta chain.

While usually the entire cytoplasmic region will be employed, in many cases, it will not be necessary to use the entire chain. To the extent that a truncated portion may find use, such truncated portion may be used in place of the intact chain.

The transmembrane domain may be the domain of the protein contributing the cytoplasmic portion, the domain of the protein contributing the extracellular portion, or a domain associated with a totally different protein. Chimeric receptors of the invention, in which the transmembrane domain is replaced with that of a related receptor, or, replaced with that of an unrelated receptor, may exhibit qualitative and/or quantitative differences in signal transduction function from receptors in which the transmembrane domain is retained. Thus, functional differences in signal transduction may be dependent not only upon the origin of the cytoplasmic domain employed, but also on the derivation of the transmembrane domain. Therefore, for the most part, it will be convenient to have the transmembrane domain naturally associated with one or the other of the other domains, particularly the extracellular domain. In some cases it will be desirable to employ the transmembrane domain of the zeta, eta, or $Fc_\epsilon R1$ gamma chains which contain a cysteine residue capable of disulphide bonding, so that the resulting chimeric protein will be able to form disulphide linked dimers with itself, or with unmodified versions of the zeta, eta, or $Fc\epsilon$ R1 gamma chains or related proteins. In some instances, the transmembrane domain will be selected to avoid binding of such domain to the transmembrane domain of the same or different surface membrane protein to minimize interactions with other members of the receptor complex. In other cases it will be desirable to employ the transmembrane domain of zeta, eta, $Fc\epsilon$ R1 gamma, or CD3-gamma, -delta, or -epsilon, in order to retain physical association with other members of the receptor complex.

The extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

Various naturally occurring receptors may also be employed, where the receptors are associated with surface membrane proteins, including cell differentiation (CD) antigens such as CD4, CD8-α, or cytokine or hormone receptors. The receptor may be responsive to a natural ligand, an antibody or fragment thereof, a synthetic molecule, e.g., drug, or any other agent which is capable of inducing a signal. Thus, in addition to CD receptors, ligands for receptors expressed on cancer cells could supply an the extracellular domain of the chimeric receptors of the invention. For example, human Heregulin (Hrg) a protein similar in structure to Epidermal Growth Factor (EGF), has been identified as a ligand for the receptor Her$_2$ which is expressed on the surface of breast carcinoma cells and ovarian carcinoma calls (Holmes et al., *Science* (1992) 256:1205–1210). The murine equivalent is the "Neu" protein (Bargman et al., *Nature* 319:226–230 (1986)). The extracellular domain of Hrg could be joined to the zeta transmembrane and cytoplasmic domains to form a chimeric construct of the invention to direct T cells to kill breast carcinoma cells.

In addition, "hybrid" extracellular domains can be used. For example, the extracellular domain may consist of a CD receptor, such as CD4, joined to a portion of an immunoglobulin molecule, for example the heavy chain of Ig.

Where a receptor is a molecular complex of proteins, where only one chain has the major role of binding to the ligand, it will usually be desirable to use solely the extracellular portion of the ligand binding protein. Where the extracellular portion may complex with other extracellular portions of other proteins or form covalent bonding through disulfide linkages, one may also provide for the formation of such dimeric extracellular region. Also, where the entire extracellular region is not required, truncated portions thereof may be employed, where such truncated portion is functional. In particular, when the extracellular region of CD4 is employed, one may use only those sequences required for binding of gp120, the HIV envelope glycoprotein. In the case in which Ig is used as the extracellular region, one may simply use the antigen binding regions of the antibody molecule and dispense with the constant regions of the molecule (for example, the Fc region consisting of the CH2 and CH3 domains).

In some instances, a few amino acids at the joining region of the natural protein may be deleted, usually not more than 10, more usually not more than 5. Also, one may wish to introduce a small number of amino acids at the borders, usually not more than 10, more usually not more than 5. The deletion or insertion of amino acids will usually be as a result of the needs of the construction, providing for convenient restriction sites, ease of manipulation, improvement in levels of expression, or the like. In addition, one may wish to substitute one or more amino acids with a different amino acid for similar reasons, usually not substituting more than about five amino acids in any one domain. The cytoplasmic domain as already indicated will generally be from about 50 to 500 amino acids, depending upon the particular domain employed. The transmembrane domain will generally have from about 25 to 50 amino acids, while the extracellular domain will generally have from about 50 to 500 amino acids.

Normally, the signal sequence at the 5' terminus of the open reading frame (ORF) which directs the chimeric protein to the surface membrane will be the signal sequence of the extracellular domain. However, in some instances, one may wish to exchange this sequence for a different signal sequence. However, since the signal sequence will be removed from the protein, being processed while being directed to the surface membrane, the particular signal sequence will normally not be critical to the subject invention. Similarly, associated with the signal sequence will be a naturally occurring cleavage site, which will also normally be the naturally occurring cleavage site associated with the signal sequence or the extracellular domain.

In the embodiments provided herein the following chimeric constructs were produced: CD8/zeta; CD4/zeta; CD4/gamma; CD4/delta and CD4/epsilon.

The present invention also describes single-chain antibody (SAb) chimeric receptors in which a SAb functions as the extracellular domain of the chimeric receptor. In contrast to previously described Ig-Ti chimeras (Becker et al., Gross et al., supra), the SAb chimeric receptors function by bypassing the normal antigen-recognition component of the T cell receptor complex, and transducing the signal generated upon antigen-receptor binding directly via the cytoplasmic domain of the molecule.

To create the SAb chimeric receptors, for example, anti-HIV immunoglobulin-zeta (Ig-$\zeta$) chimeric receptors, the following approaches may be used:

The full-length IgG heavy chain comprising the VH, CH1, hinge, CH2 and CH3 (Fc) Ig domains is fused to the cytoplasmic domain of the zeta chain via the appropriate transmembrane domain. If the VH domain alone is sufficient to confer antigen-specificity (so-called "single-domain antibodies"), homodimer formation of the Ig-$\zeta$ chimera is expected to be functionally bivalent with regard to antigen binding sites. Because it is likely that both the VH domain and the VL domain are necessary to generate a fully active antigen-binding site, both the IgH-$\zeta$ molecule and the full-length IgL chain are introduced into cells to generate an active antigen-binding site. Dimer formation resulting from the intermolecular Fc/hinge disulfide bonds results in the assembly of Ig-$\zeta$ receptors with extracellular domains resembling those of IgG antibodies. Derivatives of this Ig-$\zeta$ chimeric receptor include those in which only portions of the heavy chain are employed in the fusion. For example, the VH domain (and the CH1 domain) of the heavy chain can be retained in the extracellular domain of the Ig-$\zeta$ chimera (VH-$\zeta$). Co-introduction of a similar chimera in which the V and C domains of the corresponding light chain replace those of the Ig heavy chain (VL-$\zeta$) can then reconstitute a functional antigen binding site.

Because association of both the heavy and light V domains are required to generate a functional antigen binding site of high affinity, in order to generate a Ig chimeric receptor with the potential to bind antigen, a total of two molecules will typically need to be introduced into the host cell. Therefore, an alternative and preferred strategy is to introduce a single molecule bearing a functional antigen binding site. This avoids the technical difficulties that may attend the introduction of more than one gene construct into host cells. This "single-chain antibody" (SAb) is created by fusing together the variable domains of the heavy and light chains using a short peptide linker, thereby reconstituting an antigen binding site on a single molecule.

Single-chain antibody variable fragments (Fvs) in which the C-terminus of one variable domain (VH or VL) is tethered to the N-terminus of the other (VL or VH, respectively, (see FIG. 1A, FIG. 1B and FIG. 1C) via a 15 to 25 amino acid peptide or linker, have been developed without significantly disrupting antigen binding or specificity of the binding (Bedzyk et al. (1990) *J. Biol. Chem.*, 265:18615; Chaudhary et al. (1990) *Proc. Natl. Acad. Sci.*, 87:9491). These Fvs lack the constant regions (Fc) present in the heavy and light chains of the native antibody. In the methods of the present invention, the extracellular domain of the single-chain Ig chimeras consists of the Fv fragment which may be fused to all or a portion of the constant domains of the heavy chain, and the resulting extracellular domain is joined to the cytoplasmic domain of, for example, zeta, via an appropriate transmembrane domain that will permit expression in the host cell, e.g., zeta, CD4. The resulting chimeric molecules differ from the Fvs in that upon binding of antigen they initiate signal transduction via their cytoplasmic domain. In contrast, free antibodies and Fvs are not cell- associated and do not transduce a signal upon antigen binding. The ligand binding domain of the SAb chimeric receptor may be of two types depending on the relative order of the VH and VL domains: VH-1-VL or VL-1-VH (where "1" represents the linker) (See FIG. 1A, FIG. 1B, FIG. 1C, FIG. 2A, FIG. 2B, FIG. 2C, FIG. 2D and FID. 2E).

The SAb-zeta chimeric receptor constructs of the invention, F13, F14, F15 and F16, are depicted in FIG. 2D and FIG. 2E, respectively.

For the antibody receptor, ligands of interest may include viral proteins, for example the gB envelope glycoprotein of human cytomegalovirus, and surface proteins found on cancer cells in a specific or amplified fashion, for example the HER-2 protein which is often amplified in human breast and ovarian carcinomas. For other receptors, the receptors and ligands of particular interest are CD4, where the ligand is the HIV gp120 envelope glycoprotein, and other viral receptors, for example ICAM, which is the receptor for the human rhinovirus, and the related receptor molecule for poliovirus.

The chimeric construct, which encodes the chimeric protein according to this invention will be prepared in conventional ways. Since, for the most part, natural sequences may be employed, the natural genes may be isolated and manipulated, as appropriate, so as to allow for the proper joining of the various domains. Thus, one may prepare the truncated portion of the sequence by employing the polymerase chain reaction (PCR), using appropriate primers which result in deletion of the undesired portions of the gene. Alternatively, one may use primer repair, where the sequence of interest may be cloned in an appropriate host. In either case, primers may be employed which result in termini, which allow for annealing of the sequences to result in the desired open reading frame encoding the chimeric protein. Thus, the sequences may be selected to provide for restriction sites which are blunt-ended, or have complementary overlaps. During ligation, it is desirable that hybridization and ligation does not recreate either of the original restriction sites.

If desired, the extracellular domain may also include the transcriptional initiation region, which will allow for expression in the target host. Alternatively, one may wish to provide for a different transcriptional initiation region, which may allow for constitutive or inducible expression, depending upon the target host, the purpose for the introduction of the subject chimeric protein into such host, the level of expression desired, the nature of the target host, and the like. Thus, one may provide for expression upon differentiation or maturation of the target host, activation of the target host, or the like.

A wide variety of promoters have been described in the literature, which are constitutive or inducible, where induction may be associated with a specific cell type or a specific level of maturation. Alternatively, a number of viral promoters are known which may also find use. Promoters of interest include the β-actin promoter, SV40 early and late promoters, immunoglobulin promoter, human cytomegalovirus promoter, and the Friend spleen focus-forming virus promoter. The promoters may or may not be associated with enhancers, where the enhancers may be naturally associated with the particular promoter or associated with a different promoter.

The sequence of the open reading frame may be obtained from genomic DNA, cDNA, or be synthesized, or combinations thereof. Depending upon the size of the genomic DNA and the number of introns, one may wish to use cDNA or a combination thereof. In many instances, it is found that introns stabilize the mRNA. Also, one may provide for non-coding regions which stabilize the mRNA.

A termination region will be provided 3' to the cytoplasmic domain, where the termination region may be naturally associated with the cytoplasmic domain or may be derived from a different source. For the most part, the termination regions are not critical and a wide variety of termination regions may be employed without adversely affecting expression.

The various manipulations may be carried out in vitro or may be introduced into vectors for cloning in an appropriate host, e.g., *E. coli*. Thus, after each manipulation, the resulting construct from joining of the DNA sequences may be cloned, the vector isolated, and the sequence screened to insure that the sequence encodes the desired chimeric protein. The sequence may be screened by restriction analysis, sequencing, or the like. Prior to cloning, the sequence may be amplified using PCR and appropriate primers, so as to provide for an ample supply of the desired open reading frame, while reducing the amount of contaminating DNA fragments which may have substantial homology to the portions of the entire open reading frame.

The target cell may be transformed with the chimeric construct in any convenient manner. Techniques include calcium phosphate precipitated DNA transformation, electroporation, protoplast fusion, biolistics, using DNA-coated particles, transfection, and infection, where the chimeric construct is introduced into an appropriate virus, particularly a non-replicative form of the virus, or the like.

Once the target host has been transformed, usually, integration, will result. However, by appropriate choice of vectors, one may provide for episomal maintenance. A large number of vectors are known which are based on viruses, where the copy number of the virus maintained in the cell is low enough to maintain the viability of the cell. Illustrative vectors include SV40, EBV and BPV.

The constructs will be designed so as to avoid their interaction with other surface membrane proteins native to the target host. Thus, for the most part, one will avoid the chimeric protein binding to other proteins present in the surface membrane. In order to achieve this, one may select for a transmembrane domain which is known not to bind to other transmembrane domains, one may modify specific amino acids, e.g. substitute for a cysteine, or the like.

Once one has established that the transformed host is capable of expressing the chimeric protein as a surface membrane protein in accordance with the desired regulation and at a desired level, one may then determine whether the transmembrane protein is functional in the host to provide for the desired signal induction. Since the effect of signal induction of the particular cytoplasmic domain will be known, one may use established methodology for determining induction to verify the functional capability of the chimeric protein. For example, TCR binding results in the induction of CD69 expression. Thus, one would expect with a chimeric protein having a zeta cytoplasmic domain, where the host cell is known to express CD69 upon activation, one could contact the transformed cell with the prescribed ligand and then assay for expression of CD69. Of course, it is important to know that ancillary signals are not required from other proteins in conjunction with the particular cytoplasmic domain, so that the failure to provide transduction of the signal may be attributed solely to the inoperability of the chimeric protein in the particular target host.

A wide variety of target hosts may be employed, normally cells from vertebrates, more particularly, mammals, desirably domestic animals or primates, particularly humans. The subject chimeric constructs may be used for the investigation of particular pathways controlled by signal transduction, for initiating cellular responses employing different ligands, for example, for inducing activation of a particular subset of lymphocytes, where the lymphocytes may be activated by particular surface markers of cells, such as neoplastic cells, virally infected cells, or other diseased cells, which provide for specific surface membrane proteins which may be distinguished from the surface membrane proteins on normal cells. The cells may be further modified so that expression cassettes may be introduced, where activation of the transformed cell will result in secretion of a particular product. In this manner, one may provide for directed delivery of specific agents, such as interferons, TNF's, perforans, naturally occurring cytotoxic agents, or the like, where the level of secretion can be greatly enhanced over the natural occurring secretion. Furthermore, the cells may be specifically directed to the site using injection, catheters, or the like, so as to provide for localization of the response.

The subject invention may find application with cytotoxic lymphocytes (CTL), Natural killer cells (NK), tumor-infiltrating-lymphocytes (TIL) or other cells which are capable of killing target cells when activated. Thus, diseased cells, such as cells infected with HIV, HTLV-I or II, cytomegalovirus, hepatitis B or C virus, mycobacterium avium, etc., or neoplastic cells, where the diseased cells have a surface marker associated with the diseased state may be made specific targets of the cytotoxic cells. By providing a receptor extracellular domain, e.g., CD4, which binds to a surface marker of the pathogen or neoplastic condition, e.g., gp120 for HIV, the cells may serve as therapeutic agents. By modifying the cells further to prevent the expression or translocation of functional Class I and/or II MHC antigens, the cells will be able to avoid recognition by the host immune system as foreign and can therefore be therapeutically employed in any individual regardless of genetic background. Alternatively, one may isolate and transfect host cells with the subject constructs and then return the transfected host cells to the host.

Other applications include transformation of host cells from a given individual with retroviral vector constructs directing the synthesis of the chimeric construct. By transformation of such cells and reintroduction into the patient one may achieve autologous gene therapy applications.

In addition, suitable host cells include hematopoietic stem cells, which develop into cytotoxic effector cells with both myeloid and lymphoid phenotype including granulocytes, mast cells, basophils, macrophages, natural killer (NK) cells and T and B lymphocytes. Introduction of the chimeric constructs of the invention into hematopoietic stem cells thus permits the induction of cytotoxicity in the various cell types derived from hematopoietic stem cells providing a continued source of cytotoxic effector cells to fight various diseases. The zeta subunit of the T cell receptor is associated not only with T cells, but is present in other cytotoxic cells derived from hematopoietic stem cells. Three subunits, zeta, eta and the gamma chain of the Fcε receptor, associate to form homodimers as well as heterodimers in different cell types derived from stem cells. The high level of homology between zeta, eta and the gamma chain of the Fcε receptor, and their association together in different cell types suggests that a chimeric receptor consisting of an extracellular binding domain coupled to a zeta, eta or gamma homodimer, would be able to activate cytotoxicity in various cell types derived from hematopoietic stem cells. For example, zeta and eta form both homodimers and heterodimers in T cells (Clayton et al. (1991) *Proc. Natl. Acad. Sci. USA* 88:5202) and are activated by engagement of the cell receptor complex; zeta and the gamma chain of the Fcε receptor form homodimers and heterodimers in NK cells and function to activate cytotoxic pathways initiated by engagement of Fc receptors (Lanier et al. (1991) *J. Immunol.* 146:1571 (1991); the gamma chain forms homodimers in monocytes and macrophages (Phillips et al. (1991) *Eur. J. Immunol.* 21:895), however because zeta will form heterodimers with gamma, it is able to couple to the intracellular machinery in the monocytic lineage; and zeta and the gamma chain are used by IgE receptors (FcRI) in mast cells and basophils (Letourneur et al. (1991) *J. Immunol.* 147:2652) for signalling cells to initiate cytotoxic function. Therefore, because stem cells transplanted into a subject via a method such as bone marrow transplantation exist for a lifetime, a continued source of cytotoxic effector cells is produced by introduction of the chimeric receptors of the invention into hematopoietic stem cells to fight virally infected cells, cells expressing tumor antigens, or effector cells responsible for autoimmune disorders. Additionally, introduction of the chimeric receptors into stem cells with subsequent expression by both myeloid and lymphoid cytotoxic cells may have certain advantages in immunocompromised individuals such as patients with AIDS. This is because the maintenance of the lymphoid cytotoxic cells (CD8+) may require the continued function of helper T cells (CD4+) which are impaired in AIDS patients.

The chimeric receptor constructs of the invention are introduced into hematopoietic stem cells followed by bone marrow transplantation to permit expression of the chimeric receptors in all lineages derived from the hematopoietic system. High-titer retroviral producer lines are used to transduce the chimeric receptor constructs, for example CD4/ζ, into both murine and human T-cells and human hematopoietic stem cells through the process of retroviral mediated gene transfer as described by Lusky et al. in (1992) *Blood* 80:396. For transduction of hematopoietic stem cells, the bone marrow is harvested using standard medical procedures and then processed by enriching for hematopoietic stem cells expressing the CD34 antigen as described by Andrews et al. in (1989) *J. Exp. Med.* 169:1721. These cells are then incubated with the retroviral supernatants in the presence of hematopoietic growth factors such as stem cell factor and IL-6. The bone marrow transplant can be autologous or allogeneic, and depending on the disease to be treated, different types of conditioning regimens are used (see, Surgical Clinics of North America (1986) 66:589). The recipient of the genetically modified stem cells can be treated with total body irradiation, chemotherapy using cyclophosphamide, or both to prevent the rejection of the transplanted bone marrow. In the case of immunocompromised patients, no pre-transplant therapy may be required because there is no malignant cell population to eradicate and the patients cannot reject the infused marrow. In addition to the gene encoding the chimeric receptor, additional genes may be included in the retroviral construct. These include genes such as the thymidine kinase gene (Borrelli et al. (1988) *Proc. Natl. Acad. Sci. USA* 85:7572) which acts as a suicide gene for the marked cells if the patient is exposed to gancyclovir. Thus, if the percentage of marked cells is too high, gancyclovir may be administered to reduce the percentage of cells expressing the chimeric receptors. In addition, if the percentage of marked cells needs to be increased, the multi-drug resistance gene can be included (Sorrentino et al. (1992) *Science* 257:99) which functions as a preferential survival gene for the marked cells in the patients if the patient is administered a dose of a chemotherapeutic agent such as taxol. Therefore, the percentage of marked cells in the patients can be titrated to obtain the maximum therapeutic benefit from the expression of the universal receptor molecules by different cytotoxic cells of the patient's immune system.

The following examples are by way of illustration and not by way of limitation.

EXPERIMENTAL

Example 1

CD8/ζ chimera construction

The polymerase chain reaction, PCR (Mullis et al. (1986) *Cold Spring Harbor Symposium on Quantitative Biology*, LI, 263–273) was used to amplify the extracellular and transmembrane portion of CD8α (residues 1–187) from pSV7d-CD8α and the cytoplasmic portion of the human ζ chain (residues 31–142 from pGEM3ζ. DNA sequences are from (Littman et al. (1985) *Cell* 40:237–246; CD8), and (Weissman et al. (1988) *Proc. Natl. Yacht. Sci. USA*, 85:9709–9713; ζ). Plasmids pSV7d-CD8α and pGEM3zζ were kindly provided by Drs. Dan Littman and Julie Turner (Univ. of CA, S.F.) and Drs. R. D. Klausner and A. M. Weissman (N.I.H.), respectively. Primers encoding the 3' sequences of the CD8 fragment and the 5' sequences of the zeta fragment (ζ) were designed to overlap such that annealing of the two products yielded a hybrid template. From this template the chimera was amplified using external primers containing XbaI and BamHI cloning sites. The CD8/ζ chimera was subcloned into pTfneo (Ohashi et al. (1985) *Nature*, 316:606–609) and sequenced via the Sanger dideoxynucleotide technique (Sanger et al. (1977) *Proc. Natl. Yacht. Sci. USA*, 74:5463–5467).

Antibodies

C305 and Leu4 mAbs recognize the Jurkat Ti β chain and an extracellular determinant of CD3 ε, respectively. OKT8, acquired from the ATCC, recognizes an extracellular epitope of CD8. The anti-ζ rabbit antiserum, #387, raised against a peptide comprising amino acids 132–144 of the murine ζ sequence (Orloff et al. (1989) *J. Biol. Chem.*, 264:14812–14817), was kindly provided by Drs. R. D. Klausner, A. M. Weissman and L. E. Samelson. The anti-phosphotyrosine mAb, 4G10, was a generous gift of Drs. D. Morrison, B. Druker, and T. Roberts. W6/32 recognizes an invariant determinant expressed on human HLA Class 1 antigens. Leu23, reactive with CD69, was obtained from Becton-Dickinson Monoclonal Center (Milpitas, Calif.). MOPC 195, an IgG2a, (Litton Bionetics, Kensington, Md.) was used as a control mAb in FACS analysis. Ascitic fluids of mAb were used at a final dilution of 1:1000 (a saturating concentration) in all experiments unless otherwise stated.

Cell lines and Transfections

The human leukemic T cell line Jurkat and its derivative J.RT3-T3.5 were maintained in RPMI 1640 supplemented with 10% fetal bovine serum (FBS) glutamine, penicillin and streptomycin (Irvin Scientific). Chimera-transfected clones were passaged in the above medium with the addition of Geneticin (GIBCO, Grand Island, N.Y.) at 2 mg/ml. Electroporation of pTfneo-CD8/ζ into Jurkat and J.RT3-T3.5 was performed in a Bio-Rad Gene Pulser using a voltage of 250 V and a capacitance of 960 μF with 20 μg of plasmid per $10^7$ cells. After transfection, cells were grown for two days in RPMI before plating out in Geneticin-containing medium. Clones were obtained by limiting dilutions and screened for TCR and CD8/ζ expression by Flow Cytometry (see below). The Jurkat CD8 clone, transfected with the wild-type CD8 protein, was kindly provided by Drs. Julia Turner and Dan Littman.

Flow Cytometry

Approximately $1 \times 10^6$ cells/condition were stained with saturating concentrations of antibody, then incubated with fluorescein-conjugated goat antimouse Ab prior to analysis in a FACScan (Beckton Dickinson) as previously described (Weiss and Stobo 1984). Cells analyzed for CD69 expression were stained directly with fluorescein-conjugated Leu 23 (anti-CD69 mAb) or MOPC 195 (control mAb).

$Ca^{+2}]_i$ Measurement by Fluorimetry

Calcium sensitive fluorescence was monitored as previously described (Goldsmith and Weiss 1987 *Proc. Natl. Yacht. Sci. USA*, 84:6879–6883). Cells were stimulated with soluble mAb C305 and OKT8 at saturating concentrations (1:1000 dilution of ascites). Maximal fluorescence was determined after lysis of the cells with Triton X-100; minimum fluorescence was obtained after chelation of $Ca^{+2}$ with EGTA. $[Ca^{+2}$ was determined using the equation $[Ca^{+2}]_i = K_d (F_{observed} - F_{Min})/(F_{max} - F_{observed})$, with $K_d = 250$ nM as described (Grynkiewica et al. (1985) *J. Biol. Chem.*, 260:3440–3448).

Inositol Phosphate Measurement

Cells were loaded with [$^3$H]myo-inositol (Amersham) at 40 λCi/ml for 3 hr. in phosphate buffered saline, then cultured overnight in RPMI 1640 supplemented with 10% fetal bovine serum. Cells were stimulated for 15 min. with the indicated antibodies at 1:1000 dilution of ascites in the presence of 10 mM LiCl to inhibit dephosphorylation of $IP_1$. The extraction and quantitation of soluble inositol phosphates were as described (Imboden and Stobo (1985) *J. Exp. Med.*, 161:446–456).

Surface Iodinations

Cells were labeled with $125_I$ using the lactoperoxidase/glucose oxidase (Sigma) procedure as described (Weiss and Stobo (1984) *J. Exp. Med.*, 160:1284–1299).

Immunoprecipitations

Cells were lysed at $2 \times 10^7$ cells/200 ml in 1% NP40 (Nonidet P40), 150 mM NaCl, and 10 mM Tris pH 7.8 in the presence of protease inhibitors, 1 mM PMSF, aprotinin, and leupeptin. Lysis buffer for lysates to be analyzed for phosphotyrosine content was supplemented with phosphatase inhibitors as described (Desai et al. 1990, *Nature*, 348:66–69). Iodinated lysates were supplemented with 10 mM iodoacetamide to prevent post-lysis disulfide bond formation. Digitonin lysis was performed in 1% Digitonin, 150 mM NaCl, 10 mM Tris pH 7.8, 0.12% Triton X-100 After 30 min at 4° C., lysates were centrifuged for 10 min. at 14,000 rpm., then precleared with fixed Staphylococcus aureus (Staph A; Calbiochem-Behring). Alternatively, lysates of cells stimulated with antibody prior to lysis were precleared with sepharose beads. The precleared lysates were incubated with Protein A Sepharose CL-4B beads which had been prearmed with the immunoprecipitating antibody. Washed immunoprecipitates were resuspended in SDS sample buffer +/−5% β-mercaptoethanol and boiled prior to electrophoresis on 11% polyacrylamide gels.

Stimulation of cells for assessment of phosphotyrosine content

Cells were stimulated in serum free medium at $2 \times 10^7$ cells/200 μl with antibodies at 1:250 dilution of ascites. After 2 min. at 37° C., the medium was aspirated, and the cells lysed in 100 μl of NP40 lysis buffer. Lysates were precleared, then ultracentrifuged and samples resolved by SDS PAGE.

Immunoblots

Gels were equilibrated in transfer buffer (20 mM Tris-base, 150 mM glycine, 20% methanol) for 30 min. and transferred to nitrocellulose membranes in a Bio-Rad Western blotting apparatus run at 25 volts overnight. Membranes were blocked in TBST (10 mMTris HCl [pH 8], 150 mM NaCl, 0.05% Tween 20) plus 1.5% ovalbumin, then incubated with either mAb 4G10 or rabbit anti-ζ antiserum (#387). The immunoblots were washed and incubated with a 1:7000 dilution of alkaline phosphatase-conjugated goat anti-mouse or goat antirabbit antibody. After 1–2 hours, the blots were washed and developed with nitroblue tetrazolium and 5-bromo-4-chloro-3-indolyl phosphate substrates as per manufacturer's instructions (Promega).

IL-2 Bioassay

For stimulation, cells were coated with the indicated antibodies at saturating concentrations (1:1000 dil. of ascites) for 30 min. at 4° C. After removal of unbound antibody, cells were spun onto 24-well tissue culture plates which had been precoated with rabbit anti-mouse Ig (Zymed Labs) and blocked with medium plus 10% FBS. Phorbol myristate acetate, PMA (Sigma) and ionomycin (Calbiochem) were added to final concentrations of 10 mg/ml and 1 mM, respectively. Cell-free supernatants were harvested after 20 hr. of culture and assessed for IL-2 content utilizing the IL-2 dependent CTLL-2.20 cell line in the MTT colorimetric assay as described (Mosmann 1983, *J. Immunol. Meth.*, 65:55–63.

RESULTS

Characterization of the CD8/ζ chimera in T cell receptor-positive and -negative Jurkat cells The CD8/ζ chimeric construct described previously was transfected via electroporation into both the Jurkat human T cell leukemic line, yielding clone JCD8/ζ 2, and a Jurkat-derived mutant, JRT3.T3.5 deficient in full length Ti B chain transcripts and protein, yielding Jβ-CD8/ζ 14. Though JRT3.T3.5 expresses normal levels of Ti α and the CD3 subunits, its deficiency in Ti β expression results in the absence of TCR expression on the cell surface (Ohashi et al. (1985) *Nature*, 316:606–609). Transfection of the chimera into this cell enabled assessment of ζ's signalling phenotype without the complication of the additional TCR chains. Levels of surface expression of the chimera and TCR in stably transfected clones were quantitated by flow cytometry using mAbs which recognize either CD8 (OKT8) or the CD3 ε subunit of the TCR (Leu 4). Fluorescence histograms of these clones which both express high levels of CD8/ζ was observed; this cell was used as a control in all of the experiments. The three clones express comparable levels of CD8 epitopes and T cell receptors with the exception of Jβ-CD8/z 14, which fails to express surface TCR. Thus the CD8/ζ chimera can be expressed on the cell surface in the absence of the TCR chains.

To characterize the structure of the CD8/ζ chimeric protein, cells were surface radioiodinated, lysed in 1% NP40, and subjected to immunoprecipitation with OKT8 or a normal rabbit antiserum raised against a cytoplasmic peptide sequence of murine ζ. Under reducing conditions, antibodies against either CD8 or ζ precipitate a single protein of 34–35 kD from the chimera-transfected cell, while OKT8 precipitates a 29 kD protein representing wild-type CD8 from Jurkat CD8. Although CD8 in its normal environment has an apparent molecular weight of 32–34 kD, (Snow and Terhorst (1983), *J. Biol. Chem.*, 258:14675–14681, preliminary experiments comparing CD8 in Jurkat and a CD8-positive line, HPB.ALL, suggest that the reduction in size of CD8 observed here results from a distinct pattern of glycosylation in the Jurkat host. Under non-reducing conditions a more complex pattern of proteins is seen in immunoprecipitates of both CD8 and the CD8/ζ chimera. This complexity is characteristic of CD8 precipitates since homomultimers and heteromultimers have been previously observed (Snow and Terhorst (1983), supra). The two prominent species immunoprecipitated from JCD8/ζ 2 migrating at approximately 70 and 100 kD are likely to represent homodimers and homotrimers of the chimera. As there are no cysteine residues for the formation of disulfide linkages with the ζ portion of the chimera, any disulfide bonds formed in the chimera must occur through CD8. Therefore, any protein forming a heterodimer with CD8/ζ is likely to form one with the wild-type CD8 and thus should not account for any signalling events specifically attributable to the CD8/ζ chimera.

Non-covalent association of the chimera with endogenous CD3 gamma (γ), delta (δ), and epsilon (ε) may complicate the interpretation of signals transduced by the chimera. To determine whether removal of the extracellular and transmembrane domains of ζ is sufficient to result in its expression independent of the CD3 chains, cells were surface iodinated and lysed in digitonin, a detergent known to preserve the integrity of the TCR complex. Immunoprecipitates of the TCR in both Jurkat CD8 and the TCR-expressing chimera-transfectant JCD8/ζ 2, show identical patterns characteristic of a CD3 (Leu 4) immunoprecipitate. Though TCR-associated ζ is not well iodinated, as its extracellular domain contains no tyrosine residues for labelling, ζ immunoblots of CD3 immunoprecipitates confirm its presence under these lysis conditions. A small quantity of labelled CD3 ε is seen in the Leu 4 immunoprecipitate of the TCR deficient cell despite the fact that this same mAb failed to stain this cell. The small amount of immunoprecipitated protein seen is likely due to radiolabelling of internal CD3 ε in a small number of permeabilized or non-viable cells during the labelling procedure. More importantly, no CD3 chains are detectable in precipitates of the CD8/ζ chimera in either TCR-position or -negative cells, nor is any chimera apparent in the Leu 4 precipitate of JCD8/ζ 2. Intentional overexposure of the autoradiogram also fails to reveal TCR chains coprecipitating with the chimeras. To further address the question of coassociation of the chimera and TCR chains, the effect of antibody-induced down modulation of the TCR on chimera expression was assessed. Whereas overnight incubation of JCD8/ζ 2 with saturating amounts of C305, a mAb against an epitope of the Jurkat Ti β chain, resulted in internalization of 94% of the TCR, surface expression of the CD8/ζ chimera was unaffected. By these two independent criteria, no discernible association exists between CD8/ζ and the CD3 γ, δ, and ε chains.

To determine whether a covalent link exists between endogenous ζ and the CD8/ζ chimera, ζ immunoblot analysis was performed comparing ζ and OKT8 immunoprecipitates in Jurkat CD8 and JCD8/ζ 2. The anti-ζ antiserum immunoprecipitates both the chimera and ζ from JCD8/ζ 2, but only endogenous ζ from the Jurkat CD8 control. In contrast to the anti-ζ antiserum, OKT8 immunoprecipitates the chimera but not ζ in JCD8/ζ 2, while neither species is detected in Jurkat CDS. Collectively, the results from these experiments and those described above, argue against an interaction between the chimera and endogenous T cell receptor subunits.

Stimulation of CD8/ζ results in activation of the phosphatidylinositol and tyrosine kinase pathways To determine whether binding of the extracellular domain of CD8/ζ would result in intracellular signalling events, the ability of OKT8 to elicit an increase in cytoplasmic free calcium ($[Ca^{+2}]_i$) in chimera-transfected cells was examined. A fluorimetry tracing obtained with JCD8/ζ 2 upon stimulation of its TCE with the anti-Ti β monoclonal antibody C305 was obtained. With the addition of soluble OKT8, a substantial increase in calcium ($[Ca^{+2}]_i$) is seen, suggesting that the cytoplasmic domain of ζ is capable of coupling to signalling machinery which results in the activation of phospholipase C. The ability of the chimera to transduce a signal in cells lacking surface expression of the TCE chains was examined next. Stimulation of the TCR-negative Jβ-CD8/ζ 14 with C305 results in no detectable increase in $[Ca^{+2}]_i$; however, OKT8 is still able to elicit a strong calcium response. The lack of significant increase in $[Ca^{+2}]_i$ with OKT8 stimulation in Jurkat CD8 demonstrates that the ζ portion of the chimera is required for the elicited $[Ca^{+2}]_i$ response.

Since the increase in $[Ca^{+2}]_i$ which occurs with TCR stimulation is attributed to increases in inositol phosphates, the ability of CD8/ζ to induce $PIP_2$ hydrolysis was tested by assessing changes in total soluble inositol phosphates following stimulation with OKT8. Stimulation of CD8/ζ with OKT8 resulted in the generation of inositol phosphates in both chimera-expressing cells. In contrast, no inositol phosphates were noted with stimulation of the wild-type CD8 protein in Jurkat CD8. Stimulation of TCR in Jurkat CD8 and CD8/ζ 2 induced increases in inositol phosphates, whereas in the TCR-deficient transfectant, Jβ-CD8/ζ 14, no such increase was observed upon TCR stimulation. These results are consistent with the calcium fluorimetry data and confirm the chimera's ability to activate phospholipase C even in the absence of endogenous cell surface TCR chains.

As stimulation of the T cell receptor activates a tyrosine kinase pathway in addition to inositol phospholipid pathway, it was important to determine whether chimera stimulation would result in tyrosine kinase activation. Western blots reveal a small number of tyrosine-phosphorylated proteins existing in all three clones prior to stimulation. Upon stimulation of Jurkat CD8 and JCD8/ζ 2 with C305, (anti-Ti β), the tyrosine kinase pathway is activated as demonstrated by the induction of tyrosine phosphorylation of a number of proteins. As expected, C305 has no effect in the TCR-negative transfectant, Jβ-CD8/ζ 14. Stimulation of the chimera on both JCD8/ζ 2 and Jβ-CD8/ζ 14 with OKT8 results in the appearance of a pattern of tyrosine-phosphorylated bands indistinguishable from that seen with TCR stimulation. In contrast, stimulation through wild-type CD8 in Jurkat does not result in induction of tyrosine phosphoproteins. Thus, the CD8/ζ chimera, in the absence of Ti and CD3 γ, δ, and ε, is capable of activating the tyrosine kinase pathway in a manner analogous to that of an intact TCR.

Since JCD8/2 expresses two discernible forms of ζ on its surface, -endogenous ζ and the CD8/ζ chimera-, each of which could be stimulated independently, the specificity of receptor-induced ζ phosphorylation was addressed. Immunoprecipitates of ζ derived from the three clones, either unstimuiated, or stimulated with C305 or OKT8, were analyzed by western blotting with an anti-phosphotyrosine antibody. A small fraction of the ζ immunoprecipitates were blotted with ζ antiserum to control for differences in protein content between samples. Analysis of the lysate derived from TCR-stimulated Jurkat CD8 cells reveals a typical pattern of ζ phosphorylation with the multiplicity of bands from 16–21 kD most likely representing the varying degree of phosphorylation of the seven cytoplasmic tyrosine residues of ζ. In this experiment, a small degree of constitutive ζ phosphorylation is detected in Jurkat CD8; however, this is not augmented by stimulation of the wild-type CD8 protein. Whereas phosphorylation of ζ is seen with stimulation of the TCR in JCD8/ζ 2 though weaker than that seen in C305-stimulated Jurkat CD8, no induced phosphorylation of the chimera is apparent.

Conversely, stimulation of the CD8/ζ chimeric receptor on both JCD8/ζ 2 and Jβ-CD7/ζ 14 results in a high degree of phosphorylation of the chimera exclusively, seen as an induced broad band from 34–39 kD. This result indicates that the receptor-activated kinase responsible for phosphorylation of ζ recognizes its substrate only in a stimulated receptor complex.

Stimulation of CD8/ζ results in late events of T cell activation

T-cell activation results from the delivery of receptor-mediated signals to the nucleus where they act to induce expression of specific genes. One such gene encodes the activation antigen CD69, whose surface expression is induced within hours of T cell receptor stimulation and appears to be dependent on activation of protein kinase C (Testi et al., *J. Immunol.*, 142:1854–1860. Although the function of CD69 in T cell activation is not well understood, it provides a marker of distal signal transduction events. Flow cytometry reveals a very small degree of basal CD69 expression on unstimulated cells. Maximal levels are induced on all cells with phobol myristate acetate, PMA, an activator of protein kinase. Stimulation of the TCR results in induction of CD69 on Jurkat CD8 and JCD8/ζ 2, but not on the TCR-negative clone, Jβ-CD8/ζ 14. Moreover, stimulation of cells with OKT8 induces CD69 on both cells expressing the CD8/ζ chimera. Though a minimal degree of CD69 induction is apparent with stimulation of wild-type CD8 protein, this level is no higher than that observed with stimulation of Jurkat CD8 with a Class I MHC antibody w6/32.

Perhaps the most commonly used criterion to assess late activation events is the production of the lymphokine, interleukin-2 (IL-2) (Smith (1986) *Science*, 240:1169–1176). The IL-2 gene is tightly regulated, requiring the integration of a number of signals for its transcription, making it a valuable distal market for assessing signalling through the CD8/ζ chimera. Stimulation of Jurkat CD8 and JCD8/ζ 2 cells with TCR antibodies in the presence of PMA results in production of IL-2.

JCD8/ζ 2 and Jurkat CD8 cells were stimulated with the indicated mAb or inomycin (1 μm) in the presence of PMA (10 ng/ml). IL-2 secretion was determined by the ability of culture supernatants of stimulated cells to support the growth of the IL-2 dependent CTLL-2.20 cells. Since PMA alone induces no IL-2 production in Jurkat, yet has a small direct effect on the viability of the CTLL 2.20 cells, values obtained with PMA alone were subtracted from each response value, yielding the numbers shown above Data from two independent experiments are presented.

TABLE 1

Induction of IL-2 Production

| Treatment | IL-2 (Units/ml) | | | |
|---|---|---|---|---|
| | JCD8/ζ 2 | | | |
| | Experiment # | | Experiment # | |
| Jurkat CD8 | #1 | #2 | #1 | #2 |
| Unstimulated | <0.1 | <0.1 | <0.1 | <0.1 |
| C305 + PMA | 13.5 | 9.1 | 3.7 | 2.1 |
| OKT8 + PMA | <0.1 | <0.1 | 6.8 | 7.0 |
| C305 + OKT8 + PMA | — | — | — | — |
| W6/32 + PMA | <0.1 | <0.1 | <0.1 | <0.1 |
| Ionomycin + PMA | 30.4 | 4.2 | 24.2 | 24.6 |

Importantly, while treatment with OKT8 on Jurkat CD8 induces no IL-2, similar treatment of JCD8/2 results in levels of secreted IL-2 consistently higher than those produced in that cell with TCR stimulation. Jβ-CD8/ζ 14 responded more weakly to all experimental stimuli in this assay, but the data were qualitatively similar in that this cell reproducibly secreted IL-2 in response to OKT8 but not to C305. These data confirm that in addition to early signal transduction events, later activation events occur upon stimulation of the CD8/ζ chimera, thus demonstrating its ability to couple to the relevant signal transduction pathways in a physiologic manner.

Example 2

CD4-Zeta Chimeric Receptor In Signal Transduction

Construction of CD4-zeta Chimeras

Plasmid pGEM3zeta bears the human zeta cDNA and was provided by Dr. R. D. Klausner and Dr. S. J. Frank (NIH, Bethesda, Md.). The plasmid pBS.L3T4 bears the human CD4 cDNA, and was provided by Dr. D. Littman and Dr. N. Landau (University of California San Francisco, Calif.). A BamHi-ApaI restriction fragment (approximately 0.64 kb) encompassing the entire human zeta chain coding sequence from residue 7 of the extracellular (EXT) domain, was excised from pGEM3-zeta, and subcloned into the BamHi and ApaI restriction sites of the polylinker of pBluescript II SK (+) 9pSK is a phagemid based cloning vector from Stratagene (San Diego, Calif.), generating pSK.zeta. Subsequently, a BamHI restriction fragment encompassing the entire CD4 coding sequence (approximately 1.8 kb) was excised from pBS.L3T4, and subcloned into the BamHI site of pSK.zeta, generating pSK.CD4.zeta.

Single-stranded DNA was prepared from pSK.CD4.zeta (Stratagene pBluescript II protocol), and used as a template for oligonucleotide-mediated directional mutagenesis (Zoller and Smith, (1982) *Nucleic Acids Res.* 10:6487–6500) in order to generate CD4-zeta chimeras with the desired junctions described below (see FIG. 3A, FIG. 3B, FIG. 3C, FIG. 3D and FIG. 3E). CD4-zeta fusions 1, 2, and 3 were subsequently sequenced via the Sanger dideoxynucleotide technique (Sanger et al., *Proc. Natl. Acad. Sci.* (1977) 74:5463–5467), excised as EcoRI-ApaI restriction fragments, and cloned into the polylinker of expression vector pIK.1.1 or pIK.1.1.Neo at identical sites.

An EcoRI-BamHi restriction fragment (approximately 1.8 kb) encompassing the entire coding region of CD4 was excised from pSK.CD4.zeta, and subcloned between the EcoRI and BglII sites of the pIK.1.1 or pIK.1.1.Neo polylinker.

The plasmid pUCRNeoG (Hudziak, et al., *Cell* (1982) 31:137–146) carries the neomycin gene under the transcriptional control of the Rous Sarcoma virus (RSV) 3' LTR. The RSV-neo cassette was excised from PURC-NeoG as a HincII restriction fragment (app. 2.3 kb), and subcloned between the two SspI sites of pIK.1.1, generating pIK.1.1.Neo.

pIK.1.1 is a mammalian expression vector constructed by four successive cassette insertions into pMF2, which was created by inserting the synthetic polylinker 5'-HindIII-SphI-EcoRI-AatII-BglI-XhoI-3' into KpnI and SacI sites of pSKII (Stratagene), with loss of the KpnI and SacI sites. First, a BamHI-XbaI fragment containing the SV40 T antigen polyadenylation site (nucleotides 2770–2533 of SV40, Reddy et al., *Science* (1978) 200:494–502) and an NheI-SalI fragment containing the SV40 origin of replication (nucleotides 5725-5578 of SV40) were inserted by three-part ligation between the BglII and XhoI sites, with the loss of the BglII, BamHI, XbaI, NheI, SalI and XhoI sites. These BamHI-XbaI and NheI-SalI fragments were synthesized by PCR with pSV2Neo (Southern and Berg, *J. Mol. Appl. Gen.* (1982) 1:327-341) as the template using oligonucleotide primer pairs 5'-GGTCGACCT-GGATCCGCCATACCACATTTGTAG-3' (SEQ ID NO:35), 5'-GCCGCGGCTCTAGAGCCAGACAT-GATAAGATAC-3' (SEQ ID NO:36), 5'-AAGCTTGTGCTAGCTATCCCGCCC-CTAACTCCG-3' (SEQ ID NO:37) and 5'-CGAATTCGGTCGACCGCAAAAGC-CTAGGCCTCC-3' (SEQ ID NO:38), respectively, which incorporated BamHI, XbaI, NheI and SalI sites at their respective ends. Second, an SphI-EcoRI fragment containing the splice acceptor of the human α1 qlobin gene second exon (nucleotides +143 to +251) was inserted between the SphI and EcoRI sites. This SphI-EcoRI fragment was synthesized by PCR with pπSVαHP (Treisman et al., *Proc. Natl. Acad. Sci.* (1983) 80:7428-7432) as the template using oligonucleotide primer pairs 5'-GTCTATAG-CATGCTCCCCTGCTCCGACCCG-3' (SEQ ID NO:39) and 5'-GGTACCGAATTCTCCTGCGG-GGAGAAGCAG-3' (SEQ ID NO:40) which incorporated SphI and EcoRI sites at their respective ends. Third, the synthetic polylinker 5'-EcoRI-BglII-ApaI-AatII-3' was inserted between the EcoRI and the AatII sites. Fourth, a HindIII-SacI fragment containing the CMV IE enhancer/prompter (nucleotides -674 to -19, Boshart et al., *Cell* (1985) 41:521-530) and a SacI-SphI fragment containing the CMV IE first exon/splice donor (nucleotides −19 to +170) were inserted by three-part ligation between the HindIII and SphI sites. The HindIII-SacI fragment was prepared by PCR with pUCH.CMV (M. Calos, Stanford University, Palo Alto, Calif.) as the template using oligonucleotide primers 5'-CGCCAAGCTTGGCCATTGCATACGGT-3' SEQ ID NO:41) and 5'-GAGGTCTAGACGGTT-CACTAAACGAGCTCT-3' (SEQ ID NO:42) which incorporated HindIII and SacI sites at their respective ends. The SacI-SphI fragment was chemically synthesized.

RESULTS

Design of CD4-zeta Chimeras

Three CD4-zeta chimeric receptors (F1, F2 and F3) were constructed from the extracellular (EC) and cytoplasmic (CYT) domains of CD4 and zeta respectively. The transmembrane (TM) domains of these CD4-zeta receptors were derived from zeta (F1, F2) or CD4 (F3). F2 and F3 possess all four V domains.

Specifically:

F1 retains only the V1 and V2 of the CD4 EXT domain (residues 1-180 of the mature CD4 protein), the TM domain of zeta (residues 8-30 of the mature zeta chain) and the cytoplasmic (CYT) domain of zeta (residues 31-142 of the mature zeta chain).

F2 retains the CD4 EXT domain comprising all four V regions (residues 1-370 of the mature CD4 protein), the TM domain of the zeta chain (residues 8-30 of the mature zeta chain) and the CYT domain of zeta (residues 31-142 of the mature zeta chain).

F3 retains the CD4 EXT domain comprising all four V domains (residues 1-371 of the mature CD4 protein), the TM domain of CD4 (residues 372-395 of the mature CD4 chain), and the CYT domain of zeta (residues 31-142 of the mature zeta chain).

Transient Expression of CD4-zeta Receptors

Chimeric receptors F1, F2, and F3, and the native CD4 gene were introduced into an expression vector pIK.1.1 which directs transcription via the CMV promoter/enhancer. In order to evaluate the structural integrity and cell surface levels of expression of these chimeric receptors, a highly efficient transient expression system was employed. Constructs were introduced by electroporation into the human embryonic kidney cell line, 293 (American Type Culture Collection, ATCC, Rockville, Md.), cells were harvested 24 hours later, and subsequently analyzed by FACS employing a FITC-coupled mAb specific for the V1 domain of CD4, OKT4A. The results are summarized in FIG. 4A, FIG. 4B, FIG. 4C, FIG. 4D and FIG. 4E. Although similarly high levels of surface F2 and F3 were detected by OKT4A, the level of F1 detected by this antibody in the same transient assay was extremely low.

In order to address whether F1 was present in the membrane, and to assess the structure of the chimeric proteins, immunoprecipitation of radiolabelled proteins was carried out. 20 hours after electroporation of 293 cells with either F1, F2 or F3, cells were pulse-labelled with $^{35}$S-methionine for four hours, lysed in 1% NP40, and subjected to immunoprecipitation by either OKT4A (Ortho Pharmaceuticals, N.J.) or a rabbit antiserum raised against a cytoplasmic peptide of murine zeta (obtained from R. Klausner, NIH, Md.). The level of radiolabelled F1 relative to either F2 or F3 was significantly higher when anti-zeta antiserum instead of OKT4A was used as the immunoprecipitation agent. These results suggest that the F1 receptor may not present the necessary topology for efficient binding of V1-specific mAbs.

F1 and F2 From Disulfide-Linked Homodimers; F3 is a Monomer

Native zeta exists as a disulfide-linked homodimer or as a heterodimer in which the zeta chain is associated with an alternatively spliced product of the same gene, Eta. F1 and F2 both possess the TM domain of zeta, and therefore should have the potential to form a homodimer (and possibly a heterodimer with native zeta) via the membrane proximal cysteine residue (position 11 of the mature zeta chain). In contrast, the transmembrane domain of F3 is derived from CD4, and would therefore be expected to confer the native monomeric state of the native CD4 molecule to the F3 receptor.

In order to determine whether these receptors do form covalent linkages, immunoprecipitates of radiolabelled 293 cells which have been electroporated with each of the constructs under evaluation, were analyzed under reducing and non-reducing conditions. Under both reducing conditions, a single protein of approximately 70 kb was immunoprecipitated by OKT4A from 293 cells electroporated with F3. As expected, CD4 also gave rise to a single protein of approximately 60 kd under both reducing and non-reducing conditions. In contrast, F1 and F2 gave rise to proteins of approximately 70 kd and 150 kd, respectively under non-reducing conditions, approximately double that seen under reducing conditions (approximately 34 kd and 70 kd respectively). These results demonstrate that F1 and F2, like native zeta, exist as disulfide-linked homodimers, whereas F3 exists as a monomer, as does native CD4.

These data do not rule out the ability of F3 to form a noncovalently associated dimer.

Introduction of CD4-zeta Receptors into a Human T Cell Line

The chimeric receptor genes F1, F2, and F3, and the native CD4 gene, were introduced into a derivative of pIK.1.1 bearing a selective marker, pIK.1.1Neo. Each construct was stably introduced via electroporation into the human T cell leukemia line, Jurkat, and independent Jurkat clones obtained by limiting dilution and selection of G418. Cell surface expression of the chimeric receptor was assessed by FACS analysis of Jurkat clones employing FITC-coupled OKT4A. Although native Jurkat cells express a low level of CD4 on the cell surface, transfectants expressing high levels of F2 or F3 were readily identified due to the significantly higher levels of fluorescence observed relative to untransfected cells. Similarly, stable clones expressing high levels of CD4 were also identified. In contrast, none of the clones isolated from cells electroporated with the F1 receptor construct revealed levels of OKT-4A-specific fluorescence higher than that seen with native Jurkat cells.

FACS analysis of over 100 Jurkat clones, revealed that the F3 receptor has the potential to be stably expressed in Jurkat cells at significantly higher levels (up to 50 fold) than the F2 receptor.

Induction of CD69 Expression Upon Stimulation of Native and Chimeric Receptors

CD69 (Leu-23) is an early human activation antigen present on T, B, and NK lymphocytes. CD69 is detected on the cell surface of T lymphocytes within 2 hours after stimulation of CD3/TCR, reaching a maximal level by 18 to 24 hours. CD69 is therefore the first detectable cell surface protein induced in response to CD3/TCR-mediated signals, and represents a reliable marker of T cell activation. The ability of the CD4-zeta chimeric receptors to specifically mediate CD69 induction in the Jurkat T cell line was investigated. Representative Jurkat clones expressing either F2, F3, or CD4 were selected for functional analysis (FIG. 5A, FIG. 5B, FIG. 5C, FIG. 5D, FIG. 5E and FIG. 5F).

Figure 6:
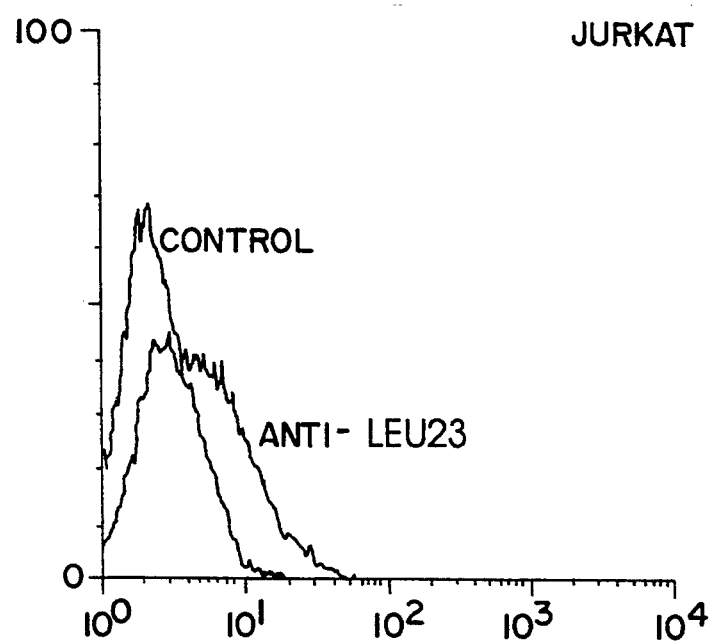
FIG. 6 is a graph of FACS analysis of basal CD69 expression of unstimulated cells as described in Example 2, infra.
Figures 9A, 9B, 9C, 9D, 9E:
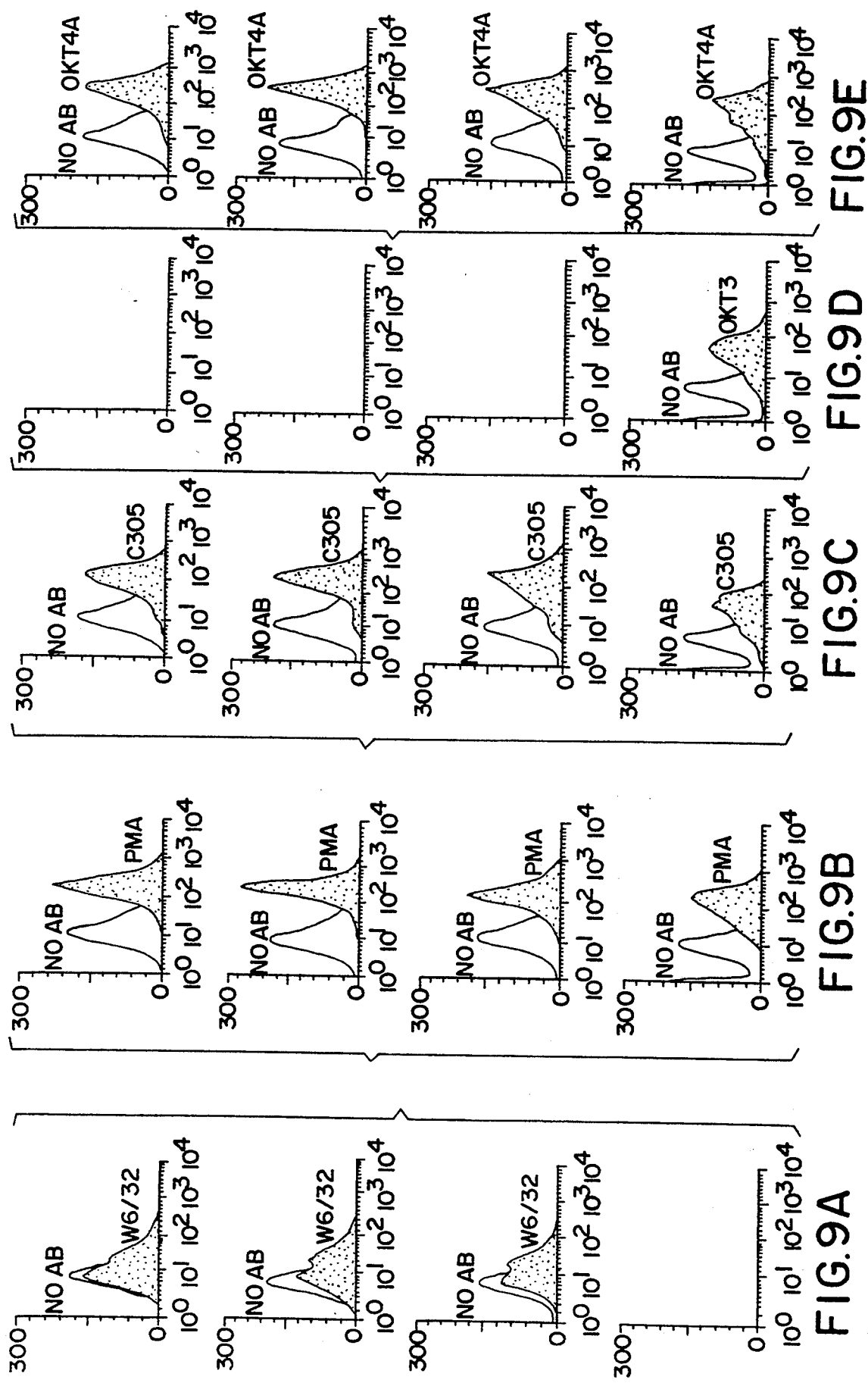
FIG. 9A, FIG. 9B, FIG. 9C, FIG. 9D and FIG. 9E are graphs of FACS analysis of CD69 expression in Jurkat cells expressing the F3 chimeric receptor, upon stimulation with various agents as described in Example 2, infra (FIG. 9A: treatment with W6/32 antibody as negative control.

Monoclonal antibodies specific for the Ti $\alpha/\beta$ or CD3 chains can mimic the effect of antigen and serve as agonists to stimulate signal transduction and T cell activation events. Cells were stimulated with immobilized mAbs specific for (a) the Ti $\beta$ chain Jurkat, (C305), (b) the CD3 $\epsilon$ chain (OKT3), and (c) the V1 domain of CD4 (OKT4A). W6/32 recognizes an invariant determinant of human HLA class 1 antigens, and was used in some experiments as negative control. CD69 expression was assayed by FACS analysis approximately 18 hours post-stimulation, employing FITC-couples anti-Leu 23 mAb. The results are summarized in FIGS. 6–9. Unstimulated cells exhibited a very low level of basal CD69 expression (FIG. 6) but upon stimulation with a pharmacological activator of protein kinase C, phorbol myristate acetate (PMA), maximal expression was induced (FIG. 7B; FIG. 8B and FIG. 9B). Stimulation of native Ti with the C305 mAb (FIG. 7C; FIG. 8C and FiG. 9C), or native CD3 with the OKT3 mAb (FIG. 7D; FIG. 8D and FIG. 9D), also resulted in induction to the CD69 marker. However, stimulation by OKT4A gave rise to a high level of CD69 expression only for those transfectants expressing a chimeric CD4-ζ receptor (FIG. 7E; FIG. 8 and FIG. 9E). Indeed, for a number of transfectants, particularly F3-derived, the level of CD69 induction observed upon stimulation was equal to that seen with PMA.

Stimulation of wild-type CD4 with OKT4A resulted in little or no induction of CD69, when assayed in a number Jurkat CD4-transfectants. Similarly, treatment of transfectants with the class 1 antibody, w6/32, had no significant effect in this assay (FIG. 7A; FIG. 8A and FIG. 9A). Furthermore, secretion of IL-2 upon stimulation with OKT4A has been observed.

These results demonstrate that CD4 chimeric receptors possessing the cytoplasmic tail of zeta function effectively in initiation of T cell activation events. Specifically, chimeric CD4-zeta receptors bearing the CD4 TM domain (F3) mediate T cell activation more efficiently (with respect to CD69 induction) than those bearing the zeta TM domain (F2), despite the fact that the latter retains the homodimeric form of native zeta.

F3 differs from F2 and native zeta, in that it does not exist in the form of a covalent homodimer. These data therefore demonstrate that covalent dimerisation of the chimeric receptor is not essential for initiation of T cell activation as measured by CD69 induction.

EXAMPLE 3

Single Chain Antibody-Zeta Chimetic Receptor

Preparation of IgG-zeta and Single-chain Antibody-zeta (SAb-ζ) Receptors

Construction of expression vector encoding the heavy chain of human monoclonal antibody (mAb) 98.6

To direct the expression of the heavy chain of human mAb 98.6 (MedImmune; S. Zolla-Pazno, *Proc. Natl. Acad. Sci.* (1989) 86:1624–1628), the plasmid pIK.98.6-γFL was constructed. A full length IgG1 heavy chain cDNA was generated by reverse transcription of 5 μg of total RNA from the cell line SP-1/98.6 (Zolla-Pazno, supra) using oligo-dT as the primer, followed by PCR using oligonucleotide primers 17 (SEQ ID NO:17) and 2 (SEQ ID NO:02). The 1.5 kb Eco RI to Bgl II fragment was cloned between the Eco RI and Bgl II sites of pIK1.1. To ensure that the heavy chain would be of the desired allotype, the Kas I-Bgl II fragment of the cDNA was replaced with a 0.94 kb Kas I - Bgl II fragment from pIK.Cγ1. pIK.Cγ1 was constructed by the insertion of a cDNA coding for the constant region of IgG1 heavy chain obtained by PCR using DNA from a human spleen cDNA library (Clontech, Inc., Palo Alto, Calif.) as substrate and oiigonucleotide primers 2 (SEQ ID NO:02) and 18 (SEQ ID NO:18), between the Eco RI and Bgl II sites of pIK1.1.

Construction of expression vector encoding the light chain of human monoclonal antibody (mAb) 98.6

To direct the expression of the light chain of mAb 98.6, the plasmid pIK.98.6κFL was constructed. A full length IgG1 light chain cDNA was generated by reverse transcription of 5 μg of total RNA from the cell line SP-1/98.6 using pdN$_6$ (Pharmacia/LKB) as the primer, followed by PCR with primers 19 (SEQ ID NO:48) and 20 (SEQ ID NO:20). The 0.78 fragment was then cut with Eco RI and Bgl II and cloned between the Eco RI and Bgl II sites of pIK1.1.

Construction of expression vector encoding SAb derived from the heavy and light chains of mAb 98.6 a) Construction of pIK98.6-K/L/H

To direct the expression of a single-chain antibody (SAb) form of mAb 98.6, pIK.98.6-K/L/H was constructed. The SAb expressed consists of the secretion leader sequence and amino acids 1–107 of the mature 98.6 mAb light chain variable ($V_L$) region fused to a 14 amino acid linker of the sequence GSTSGSGSSEGKG (L212, Betzyk et al., *J. Biol. Chem.* (1990) 265:18615–18620) which in turn is fused to amino acid 1 of the mature 98.6 mAb heavy chain $V_H$ region. This is then fused at amino acid 113 to amino acid 234 of the IgG1 heavy chain constant region, in order to delete the CH1 domain of the IgG1 heavy chain constant region for improved secretion. pIK.98.6-K/L/H was constructed in three steps.

First, deletion mutagenesis was performed to fuse amino acid 113 of the $V_H$ region of mAb 98.6 to amino acid 234 of the IgG1 heavy chain, using the single stranded template form of pIK.98.6-γFL as the template and oligonucleotide 21 (SEQ ID NO:21) as primer. Correctly deleted plasmids were found using oligonucleotide 22 (SEQ ID NO:22) as a probe. This plasmid is referred to as pIK.H/Fc-int. To fuse amino acid 107 to the amino terminus of the linker peptide, the $V_L$ region of the mAb 98.6 light chain was generated by PCR using pIK.98.6-κFL as substrate and oligonucleotides 23 (SEQ ID NO:23) and 24 as primers. This was done to place a Sal I site at the 3′ end of the $V_L$ sequence, without altering the amino acid sequence of the resulting protein. This fragment, together with oligonucleotides 25 (SEQ ID NO:25) and 26 (SEQ ID NO:26) was ligated between the EcoRI and Bgl II sites of pIK1.1, generating the plasmid pIK.K/L-int.

In the final step, the 0.45 kb fragment of pIK.K/L-int was cloned between the Eco RI and Kpn I sites of pIK.H/Fc-int., generating plasmid pIK.K/L/H-int. Single stranded DNA from this plasmid was used as template and oligonucleotide 27 (SEQ ID NO:28) was used as primer to fuse the carboxy-terminal amino acid of the linker to amino acid 1 of the $V_H$ region of mAb 98.6 by deletion mutagenesis. Correctly deleted plasmids were found using oligonucleotide 28 as a probe. The resulting plasmid is pIK.98.6K/L/H.

Construction of an expression vector expressing an alternative SAb form of mAb 98.6, pIK98.6-H/L/K To direct the expression of an alternative SAb form of mAb 98.6, pIK.98.6-H/L/K was constructed. The SAb expressed consists of the secretion leader sequence and amino acids 1–113 of mature 98.6mAb heavy chain $V_H$ region fused to a 15 amino acid linker of the sequence GGGGSGGGGSGGGGS (SEQ ID NO:43) (Choudhary et al., (1990) *Proc. Natl. Acad. Sci.* 87:9491) fused to amino acid 1 of the mature 98.6 mAb light chain $V_L$ region. This is then fused at amino acid 107 to amino acid 234 of the IgG1 heavy chain constant region, deleting the CH1 domain of IgG1 for improved secretion. pIK.98.6-H/L/K was constructed in three steps.

First, the 0.78 kb Eco RI to Nhe I fragment of pIK.98.6-κ-FL was cloned between the Eco RI and NHe I sites of pIK.CD4γ1. pIK.CD4γ1 contains a cDNA coding for a fusion of the CD4 molecule to the constant region of IgG1 heavy chain. The resulting plasmid, pIK.K/CD4/Fc-int. was used in single stranded form as template and oligonucleotide 29 (SEQ ID NO:29) was used as primer to fuse amino acid 107 of the mAb 98.6 light chain to amino acid 234 of the IgG1 heavy chain constant region by deletion mutagenesis. Correctly deleted plasmids were found using oligonucleotide 30 (SEQ ID NO:30) as a probe. The resulting plasmid is referred to as pIK.K/Fc-int.

To fuse amino acid 113 of the mAb 98.6 heavy chain to the amino terminal amino acid of the linker, the $V_H$ region was generated by PCR using pIK.98.6-γFL as substrate and oligonucleotides 24 (SEQ ID NO:24) and 31 (SEQ ID NO:31) as primers. This was done to place an Xho I site at the 3′ end of the $V_H$ sequence without altering the amino acid sequence of the resulting protein. This fragment, together with oligonucleotides 32 (SEQ ID NO:32) and 33 (SEQ ID NO:33) was ligated between the Eco RI and Bgl II sites of pIK1.1, generating the plasmid pIK.H/L-int.

Finally, the 0.5 kb Eco RI to Mlu I fragment of pIK.H/L-int. was cloned between the Eco RI and Mlu I sites of pIK.K/Fc-int., generating the plasmid pIK.K/L/H-int. Single stranded DNA from this plasmid was used as template and oligonucleotide 34 (SEQ ID NO:34) was used as the primer to fuse the carboxyterminal amino acid of the linker to amino acid 1 of the $V_L$ region of mAb 98.6 by deletion mutagenesis. Correctly deleted plasmids were found using oligonucleotide 35 (SEQ ID NO:35) as a probe. The resulting plasmid is pIK.98–6H/L/K.

Construction of expression vectors encoding IgG$_H$-zeta fusions:

a) Construction of pIK.F11

To direct the expression of a fusion protein consisting of the full-length mAb 98–6 heavy chain (amino acids -19–444), linked by the 18 amino acid IgG3 M1 membrane hinge to the ζ transmembrane and cytoplasmic domains (amino acids 10–142), pIK.F11 was constructed by inserting the 1.4 kb Eco RI to Nsi I fragment of pIK.98–6γFL, together with the 0.74 kb Nsi I to Apa I fragment of pIK.F5 between the Eco RI and Apa I sites of pIK1.1.

b) Construction of pIK.F12

To direct the expression of a fusion protein consisting of the full-length mAb 98–6 heavy chain (amino acids -19–444), linked by the 18 amino acid IgG3 M1 membrane hinge to the CD4 transmembrane (amino acids 372–395) and ζ cytoplasmic domains (amino acids 31–142), pIK.F12 was constructed by inserting the 1.4 kb Eco RI to Nsi I fragment of pIK.98-6γFL, together with the 0.74 kb Nsi I to Apa I fragment of pIK.F7 between the Eco RI and Apa I sites of pIK1.1.

Construction of expression vectors encoding SAb-zeta fusions a) Construction of pIK.CD4γ1

The plasmid pIK.CD4γ1 was constructed to direct the expression of a fusion protein composed of the secretion leader and the first 180 amino acids of the mature CD4 antigen fused to amino acid 234 of the human IgG1 heavy chain constant region and thus containing part of the hinge and all of the CH2 and CH3 domains. This deletes the CH1 domain of IgG1 heavy chain for improved secretion. pIK.CD4γ1 was constructed by generating a fragment containing the Fc portion of the human IgG1 heavy chain by PCR using DNA from a human spleen cDNA library (Clontech) as substrate and oligonucleotides 1 (SEQ ID NO:01) and 2 (SEQ ID NO:02) as the primers. The 0.75 kb Nhe I to Bgl II fragment thus generated was ligated together with the 0.6 kb Eco RI to Nhe I fragment from pSKCD4ζ between the Eco RI and Bgl II sites of pIK1.1.

b) Construction of pIK.CD4γ2

The plasmid pIK.CD4γ2 was constructed to direct the expression of a fusion protein composed of the secretion leader and the first 180 amino acids of the mature CD4 antigen fused to amino acid 234 of the human IgG2 heavy chain constant region and thus containing part of the hinge and all of the CH2 and CH3 domains. This deletes the CH1 domain of the IgG2 heavy chain for improved secretion. pIK.CD4γ2 was constructed by generating a fragment containing the Fc portion of the human IgG2 heavy chain by PCR using DNA from a human spleen cDNA library (Clontech) as substrate and oligonucleotides 3 (SEQ ID NO:03) and 4 (SEQ ID NO:04) as the primers. The 0.75 kb Nhe I to Bgl II fragment generated was ligated together with the 0.6 kb Eco RI to Nhe I fragment from pSKCD4ζ between the Eco RI and Bgl II sites of pIK1.1.

c) Construction of pIK.F5 and pIK.F7

The plasmids pIK.F5 and pIK.F7 were constructed to direct expression of several versions of CD4/IgG-/zeta (ζ) fusion proteins which all contained a human membrane-bound IgG membrane hinge domain (Tyler et al. (1982) *Proc. Natl. Acad. Sci.* 79:2008–2012) but differed in their transmembrane domains. Each protein to be expressed contained amino acids 1–180 of CD4 receptor, followed by amino acids 234–445 of human IgG2 heavy chain constant region, followed by the 18 amino acid M1 membrane hinge domain of human IgG3 (Bensmana and Lefranc, (1990) *Immunogenetics* 32:321–330), followed by a transmembrane domain, followed by amino acids 31–142 of the human ζ chain. pIK.F5 contains the transmembrane domain (amino acids 10–30) of ζ. pIK.F7 contains the transmembrane domain (amino acids 372–395) of CD4.

To construct these plasmids, the first step was cloning the human IgG3 M1 exon (Bensmana and Lefranc, supra). This was done by generating a 0.13 kb Bam HI to Bgl II fragment containing the M1 exon by PCR using DNA from the human cell line W138 as substrate and oligonucleotides 7 (SEQ ID NO:07) and 8 (SEQ ID NO:08), and cloning it into the Bgl II site of pIK.CD4γ2. The resulting plasmid is referred to as pIK.CH3/M1-int. Single stranded DNA from this plasmid was used as template and oligonucleotide 9 (SEQ ID NO:09) was used as the primer to fuse amino acid 445 of human IgG2 to the first amino acid of the IgG3 membrane hinge domain by deletion mutagenesis. The fusion is designed to generate the sequence found at the natural junction between CH3 and M1 in membrane-bound IgG molecules. Correctly deleted clones were found using oligonucleotide 10 (SEQ ID NO:10) as a probe. The resulting plasmid is referred to as pIK.CD4γ2/M1.

Next, the 0.83 kb Nhe I to Bgl II fragment of pIK.CD4γ2/M1 was cloned together with the 0.64 kb Bam HI to Apa I fragment of pGEMζ between the Nhe I and Apa I sites of pIK.CD4γ2 resulting in the plasmid pIK.F5/F6-int. Single stranded DNA from this plasmid was used as template and oligonucleotide 11 (SEQ ID NO:11) was used as the primer to fuse the last amino acid of the M1 membrane hinge domain to amino acid 10 of ζ by deletion mutagenesis. Correctly deleted clones were found by using oligonucleotide 12 (SEQ ID NO:12) as a probe. The resulting plasmid is pIK.F5.

pIK CD4γ2/M1 was cut with Bgl II and blunted with T4 polymerase, then cut with Nhe I. The resulting 0.83 kb fragment was ligated together with the 1.3 kb Pvu II to Apa I fragment from pIK.F3 between the Nhe I and Apa I sites of pIK.CD4γ2 to generate the plasmid pIK.F7-int. Single stranded DNA from this plasmid was used as template and oligonucleotide 15 (SEQ ID NO:15) was used as the primer to fuse the last amino acid of the IgG3 M1 membrane hinge domain to amino acid 372 of CD4 by deletion mutagenesis. Correctly deleted clones were found by using oligonucleotide 16 (SEQ ID NO:16) as a probe. The resulting plasmid is pIK.F7.

d) Construction of pIK.F13neo and pIK.14neo

To direct the expression of a fusion protein consisting of the H/L/K SAb form of mAb 98.6 linked at amino acid 445 of the IgG1 heavy chain to the 18 amino acid IgG3 M1 membrane hinge, which in turn is fused to the ζ transmembrane and cytoplasmic domains (amino acid 10–142), pIK.F13neo was constructed by inserting the 1.5 kb Nsi I fragment of pIK.98.6-H/L/K between the Nsi I sites of pIK.F5 neo and a clone of the correct orientation was chosen.

To direct the expression of a fusion protein consisting of the H/L/K SAb form of mAb 98.6 linked at amino acid 445 of the IgG1 heavy chain to the 18 amino acid IgG3 M1 membrane hinge, which is in turn fused to the CD4 transmembrane (amino acids 372–395) and ζ cytoplasmic domains (amino acids 31–142), pIK.F14neo was constructed by inserting the 1.5 kb Nsi I fragment of pIK.98.6-H/L/K between the Nsi I sites of pIK.F7neo and a clone of the correct orientation was chosen.

e) Construction of pIK.F15neo and pIK.16neo

To direct the expression of a fusion protein consisting of the K/L/H SAb form of mAb 98.6 linked at amino acid 445 of the IgG1 heavy chain to the 18 amino acid IgG3 M1 membrane hinge, which is in turn fused to the ζ transmembrane and cytoplasmic domains (amino acids 10–142), pIK.F15neo was constructed by inserting the 1.5 kb Nsi I fragment of pIK.98.6-K/L/H between the Nsi I sites of pIK.F5neo and a clone of the correct orientation was chosen.

To direct the expression of a fusion protein consisting of the K/L/H SAb form of mAb 98.6 linked at amino acid 445 of the IgG1 heavy chain to the 18 amino acid IgG3 M1 membrane hinge, which is in turn fused to the CD4 transmembrane domain (amino acids 372–395) and ζ cytoplasmic domain (amino acids 31–142), pIK.F16neo was constructed by inserting the 1.5 kb Nsi I fragment of pIK.98.6-K/L/H between the Nsi I sites of pIK.F7 neo and a clone of the correct orientation was selected.

Introduction of SAb-zeta Chimeric Receptors into a Human T Cell Line

Expression vectors encoding the chimeric receptors F13, F14, F15 and F16 (pIK.F13neo, pIK.F14neo, pIK.F15neo and pIK.F16neo prepared as described above, see FIG. 2D and FIG. 2E) were stably introduced via electroporation into the human T cell leukemia line Jurkat (provided by Dr. A. Weiss, University of California, San Francisco, Calif.) and independent Jurkat clones were obtained by limiting dilution and selection in G418 antibiotic. Cell surface expression of the SAb receptor was assessed by FACS analysis of Jurkat clones employing anti-Fcγ1 and FITC-coupled anti-Ig antibodies. Several clones were identified as expressing low, but detectable levels of SAb-zeta receptor on the cell surface.

Induction of CD69 Expression upon Cross-linking of SAb-ζ Receptors

As described above in Example 1, CD69 expression was induced on the cell surface of T lymphocytes upon cross-linking of the native TCR complex with specific antibodies. The ability of the SAb-ζ chimeric receptors to activate this signal transduction pathway upon cross-linking was used an indicator of the potential of these receptors to initiate T cell activation events upon interaction with target cells expressing appropriate antigen on the cell surface.

CD69 experiments were carried out with the chimeric receptor clones as described in Example 1 for the F2 and F3 receptors. Cells were treated with the following reagents: 1) immobilized mAb specific for the native TCR complex; anti-CD3ε (OKT3) as a positive control; 2) immobilized mAb specific for the Fc domain of the SAb-ζ dimer; 3) immobilized non-specific mouse IgG1 as a negative control; and 4) a pharmacological activator of protein kinase C, phorbol myristate acetate (PMA) as a positive control.

Jurkat clones expressing F13 and F15 did not respond to anti-Fc mAb, although cross-linking of the native TCR and addition of PMA did result in induction of CD69. In contrast, clones expressing F14 and F16 were found which did induce CD69 expression upon anti-Fc mAb treatment. As expected, native Jurkat cells did not respond to anti-Fc antibodies. Differences in the ability to respond to anti-Fc mAb may reflect differences in the level of receptor expressed on the cell surface of different clones and/or the source of the transmembrane domain.

These data demonstrate the ability of chimeric SAb-ζ receptors to initiate signal transduction upon cross-linking.

EXAMPLE 4

Antigen Specific Activation of Cells Expressing Anti-HIV Universal Receptors

This example describes experiments in which two different classes of anti-HIV receptors, namely CD4-ζ and SAb-ζ, are analyzed for their functional potential as determined by their ability to stimulate IL2 production in response to 1) receptor-specific monoclonal antibodies (mAbs) and 2) co-incubation with cell lines expressing the appropriate target antigen, i.e. the env protein of HIV.

Jurkat Cells Expressing CD4-ζ and SAb-ζ Receptors

Jurkat (JK) clones expressing the different classes of anti-HIV chimeric receptors, i.e. CD4-ζ and SAb-ζ, are described above (see Example 2 and Example 3). JK clones F2/1D1 and F2/1A11 express the CD4-ζ which bears the zeta transmembrane domain. JK clones F3/2.2 and F3/2.7 express the CD4-ζ receptor which bears the CD4 transmembrane domain. JK clones CD4/1F7 and CD4/4.1 were transfected with the native CD4 receptor, and therefore express high levels of CD4 compared to native JK cells. JK clones F15.16 and F15.28 express the VL-VH.SAb-ζ receptor which bears the zeta transmembrane domain. Jurkat clones F16.6 and F16.22 express the VL-VH.SAbζ receptor which bears the CD4 transmembrane domain (see FIG. 2C, FIG, 2D and FIG. 2E).

Generation of Human Cell Lines Expressing the HIV env gene

The HIV env glycoprotein, gp160, undergoes intracellular cleavage to form the external gp120 and gp41 membrane-associated envelope components. A human cell line expressing gp160 was selected to act as a target for human T cells (i.e. Jurkat cells) expressing the anti-HIV receptors CD4-ζ and anti-gp41 SAb-ζ.

The pIK1.1 expression vector (as described in Example 2 above) was used. pIK1.1neo bears the bacterial neogene and therefore confers resistance to G418 when expressed in mammalian cells. The pCMVenv vector (obtained from Dr. D. Rekosh, University of Virginia, Va.) bears DNA sequences isolated from the HIVHXB2 clone of HIV-1 which encompass the gp160 gene. Expression of both the rev and env protein is directed form the simian CMV immediate early promoter in this vector.

To generate cell lines expressing the relevant HIV antigen for use as target cells, the human embryonic kidney cell line, 293, was simultaneously electroporated with the vectors pIK1.1neo and pCMVenv at a mass ratio of 1:20. G418-resistant clones were selected over a 2 week period, expanded and analyzed for HIV env expression by Western analysis, employing an mAb specific for an epitope in the gp120 moiety of env. Two representative clones, 293.13 and 293.18, were subsequently chosen as suitable env-expressing targets. The 293.neo clone was derived from 293 cells by electroporation of the pIK1.1neo plasmid alone, and served as a negative control in these studies.

Use of Receptor-Specific mAbs to Stimulate Activation of Jurkat Cells Expressingq CD4-ζ Chimeric Receptors, F2 and F3.

The following mAbs were employed as agents to stimulate signal transduction via the native T cell receptor or the chimeric anti-HIV receptor: mAb OKT3 (Ortho Pharmaceutical Corp., Raritan, N.J.) is specific for the CD3-ε chain of the T cell receptor complex; mAb OKT4A (Ortho) is specific for an epitope in the V1 domain of the CD4 receptor; W6/32 recognizes an invariant determinant of human HLA class 1 antigens, and served as a negative control.

JK clones, expressing CD4, F2, or F3, were resuspended at a cell density of $8 \times 10^6$/ml in growth media and placed on ice. The relevant mAb was added to 100 μl aliquots of JK cells at a final concentration of 10 μg/ml and incubated on ice for 30 minutes. After washing three times to remove unbound mAb, $4 \times 10^5$ cells were then plated out per well of 96-well microtiter plate which had been pre-coated with sheep anti-mouse IgG. Phorbol myristate acetate (PMA) was added at a final concentration of 5 ng/ml. Ionomycin was present at a final concentration of 1 μM in positive control wells. Cells were incubated at 37° C./5% $CO_2$ for 18 to 24 hours. Following the co-incubation period, supernatants were removed and assayed for IL2 concentration by solid-phase ELISA (R and D Systems, Minneapolis, Mo.). Results are summarized below in Table 2.

TABLE 2

| JURKAT CLONES | IONO | OKT4A | OKT3 | W6/32 |
| --- | --- | --- | --- | --- |
| CD4/1F7 | 100(5571) | 0.3( 19) | 38(2096) | 0.1(3) |
| CD4/4.1 | 100( 475) | 2( 9) | 65( 309) | 0.7(3) |
| F2/1D1 | 100(1138) | 60( 683) | 59( 671) | 11(123) |

TABLE 2-continued

| JURKAT CLONES | IONO | OKT4A | OKT3 | W6/32 |
|---|---|---|---|---|
| F2/1A11 | 100(1070) | 86( 543) | 51( 918) | 10(104) |
| F3/2.2 | 100( 738) | 160(1199) | 65( 481) | 3( 19) |
| F3/2.7 | 100( 320) | 210( 671) | 92( 295) | ( 0) |

Numbers reflect levels of IL2 produced relative to stimulation with Ionomycin for each Jurkat (JK) clone.
Numbers in parentheses reflect absolute levels of IL2 produced (pg/ml).

As shown by the above results, the CD4-ζ receptors F2 and F3 both mediated IL2 production in response to stimulation by immobilized mAbs specific for the CD4 extracellular domain. Cross-linking of the native CD4 receptor alone did not result in production of IL2, although the native T cell receptors in the JK.CD4 clones were fully functional as shown by their response to OKT3.

Use of Cell Lines Expressing Target Antigen $1 \times 10^5$ Cells from each of the JK clones expressing CD4 only (1F7 and 4.1), CD4-ζ constructs F2 (1D1 and 1A11) and F3 (2.2 and 2.7), and SAb-ζ constructs F15 (15.16 and 15.28) and F16 (16.60 and 16.22), were mixed with $2 \times 10^4$ target cells per well of a 96-well plate. Cells were then incubated at 37° C/5% $CO_2$ for 18 to 24 hours in the presence of 5 ng/ml PMA. The two gp 160-expressing cell lines 293.13 and 293.18 were employed as target cells in each case, and the cell line 293.neo was employed as a negative control. Following the co-incubation period, supernatants were removed and assayed for IL2 concentration by solid-phase ELISA (R and D Systems). The results are shown in Table 3.

TABLE 3

| JURKAT CLONES | NEO | #13 | #18 |
|---|---|---|---|
| CD4/1F7 | 0 | 0 | 1 |
| CD4/4.1 | 0 | 0 | 0 |
| F2/1D1 | 10 | 81 | 95 |
| F2/1A11 | 25 | 222 | 206 |
| F3/2.2 | 1 | 18 | 28 |
| F3/2.7 | 0 | 3 | 6 |
| F15.16 | 37 | 97 | 284 |
| F15.28 | 23 | 129 | 5 |
| F16.60 | 153 | 417 | 395 |
| F16.22 | 11 | 43 | 103 |

Levels of IL2 (pg/ml) produced in response to coincubation with cells not expressing HIV env (Neo), or to cells expressing HIV env (#13 and #18).
Jurkat clones are as described above.

The CD4-ζ receptors F2 and F3 both mediated IL2 production in response to stimulation by membranebound gp120. However, F2 appears to be more efficient in mediating this response as compared to F3. This appears to be in contrast to the results obtained when stimulating the chimeric receptors with anti-CD4 mAbs (see Table 1).

The anti-gp41 SAb-ζ receptors F15 and F16 mediated antigen-specific T cell activation as determined by their ability to initiate IL2 production in response to membrane-bound gp41. The levels of IL2 produced by JK clones expressing F15 and F16 were equal to or greater than the levels produced by JK clones expressing the CD4-ζ receptor, F2.

These results demonstrate the functionality of chimeric T cell receptors in which the signalling domain is derived from the T cell receptor-associated chain, zeta, and the extracellular domain is derived from an antibody. Moreover, the results demonstrate the ability of single-chain antibodies to function in signal transduction, when expressed as a membrane-bound fusion protein with a signalling domain such as zeta.

EXAMPLE 5

Construction of CD4-CD3γ, CD4-CD3δ, and CD4-CD3ε Chimeric Receptors

Cloning of CD3 chains: gamma (γ), delta (δ), and epsilon (ε)

cDNA sequences encompassing the transmembrane and cytoplasmic domains of the gamma, delta and epsilon chains were isolated by standard PCR techniques from Jurkat cell RNA using the following primer pairs:

CD3ε: 5'—GATCATGGCGCCAGAACTGCATGGAGATGG—3'  (SEQ ID NO: 44)
       5'—GATCATGGGCCCAGTGTTCTCCAGAGGGTC—3';  (SEQ ID NO: 45)

CD3δ: 5'—GATCATGGCGCCAGAGCTGTGTGGAGCTG—3'  (SEQ ID NO: 46)
       5'—GATCATGGGCCCGCCACCAGTCTCAGGTTC—3';  (SEQ ID NO: 47)

and

CD3γ: 5'—GATCATGGCGCCAGAACTGCATTGAACTA—3'  (SEQ ID NO: 48)
       5'—GATCATGGGCCCACTCTGAGTCCTGAGTTC—3'.  (SEQ ID NO: 49)

Construction of chimeric CD4-CD3ε, —CD3δ, and —CD3γ receptors

The PCR products obtained were digested with NarI and ApaI, and the resulting NarI-ApaI restriction fragments (γ=276 bp, ε=276 bp, ε=305 bp) were subcloned into the expression vector pIK1.1 CD4 (as described above in Example 2) between unique NarI and ApaI sites. Oligonucleotide-mediated deletion mutagenesis was used to generate chimeric receptors with the following compositions:

1. CD4-CD3γ

(i) CD4 extracellular and transmembrane domain (CD4 amino acids 1-395) and CD3γ cytoplasmic domain (CD3γ amino acids 117-160);

(ii) CD4 extracellular domain (CD4 amino acids 1-370) and CD3γ transmembrane and cytoplasmic domains (CD3γ amino acids 83-160).

2. CD4-CD3δ

(i) CD4 extracellular and transmembrane domain (CD4 amino acids 1-395) and CD3δ cytoplasmic domain (CD3δ amino acids 107-150);

(ii) CD4 extracellular domain (CD4 amino acids 1-370) and CD3δ transmembrane and cytoplasmic domains (CD3δ amino acids 73-150).

3. CD4-CD3ε

(i) CD4 extracellular and transmembrane domain (CD4 amino acids 1–395) and CD3ε cytoplasmic domain (CD3ε amino acids 132–185);

(ii) CD4 extracellular domain (CD4 amino acids 1–370) and CD3ε transmembrane and cytoplasmic domains (CD3ε amino acids 98–185).

It is evident from the above results that one can provide for activation of various signalling pathways in a host cell by providing for expression of a chimeric protein, which may serve as a surface membrane protein, where the extracellular domain is associated with a ligand of interest, while the cytoplasmic domain, which is not naturally associated with the extracellular domain, can provide for activation of a desired pathway. In this manner, cells can be transformed so as to be used for specific purposes, where cells will be activated to a particular pathway by an unnatural ligand. This can be exemplified by using CD4 as the extracellular domain, where binding of an HIV protein can result in activation of a T-cell which can stimulate cytotoxic activity to destroy infected cells. Similarly, other cells may be modified, so as to be more effective in disease treatment, or to immune effects and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. Chimeric DNA sequence encoding a membrane bond protein, said chimeric DNA comprising in reading frame:
   a DNA sequence encoding a signal sequence which directs the membrane bound protein to the surface membrane;
   a DNA sequence encoding a non-MHC restricted extracellular binding domain of a surface membrane protein selected from the group consisting of CD4, CD8, immunoglobulin and single-chain antibody that binds specifically to at least one ligand, wherein said ligand is a protein on the surface of a cell or a viral protein;
   a transmbembrane domain from a protein selected from the group consisting of CD4, CD8, immunoglobulin, single-chain antibody, the CD3 zeta chain, the CD3 gamma chain, the CD3 delta chain and the CD3 epsilon chain; and
   a cytoplasmic signal-transducing domain of a protein that activates an intracellular messenger system selected from the group consisting of the CD3 zeta chain, the CD3 gamma chain, the CD3 delta chain and the CD3 epsilon chain,
   wherein said extracellular domain and cytoplasmic domain are not naturally joined together and said cytoplasmic domain is not naturally joined to an extracellular ligand-binding domain, and when said chimeric DNA is expressed as a membrane bound protein in a selected host cell under conditions suitable for expression, said membrane bond protein initiates signalling in said host cell.

2. DNA according to claim 1 wherein said extracellular domain is the heavy chain of an immunoglobulin, by itself or in conjunction with a light chain, or truncated portioins of said heavy chain and said light chain containing ligand binding activity.

3. DNA according to claim 1 wherein said extracellular domain in CD8.

4. DNA according to claim 1 wherein said extracellular domain is CD4.

5. DNA according to claim 4 wherein said extracellular domain is a single-chain antibody, or portion thereof containing ligand binding activity.

6. A DNA sequence according to claim 5, wherein said single-chain antibody recognizes an antigen selected from the group consisting of viral antigens and tumor cell associated antigens.

7. A DNA sequence according to claim 6 wherein said single-chain antibody is specific for the HIV env glycoprotein.

8. A DNA sequence according to claim 3, 4 or 7 where said cytoplasmic domain is zeta.

9. A DNA sequence according to claim 1, wherein said transmembrane domain is naturally joined to said extracellular domain.

10. A DNA sequence according to claim 1, wherein said transmembrane domain is naturally joined to said cytoplasmic domain.

11. An expression cassette comprising a transcriptional initiation region, a DNA sequence according to claim 1 under the transcriptional control of said transcriptional initiation region, and a transcriptional termination region.

12. An expression cassette according to claim 9, wherein said transcriptional initiation region is functional in a mammalian host.

13. A retroviral RNA or DNA construct comprising an expression cassette according to claim 12.

14. A cell comprising a DNA sequence according to claim 1.

15. A cell according to claim 14, wherein said cytoplasmic domain is the CD3 zeta chain.

16. A cell according to claim 15, wherein said extracellular domain is the heavy chain of an immunogloboulin itself or in conjunction with a light chain, or truncated portions thereof containing ligan finding activity 17. A cell according to claim 15 wherein said extracellular domain is CD8.

18. A cell according to claim 15, wherein said extracellular domain is CD4.

19. A cell according to claim 14, wherein said cell is a mammalian cell.

20. A cell according to claim 19, wherein said mammalian cell is a human cell.

21. A cell according to claim 14 wherein said cell is a hematopoietic stem cell.

* * * * *

Disclaimer 5,359,046—Daniel J. Capon, Hillsborough; Authur Weiss, Mill Valley; Brian A. Irving; Margo R. Roberts, both of San Francisco; Krisztina Zsebo, Woodside, all of Calif. CHIMERIC CHAINS FOR RECEPTOR-ASSOCIATED SIGNAL TRANSDUCTION PATHWAYS. Patent dated Oct. 25, 1994. Disclaimer filed March 12, 1998, by the assignee, Cell Genesys, Inc. and The Regents of the University of California.

Hereby enters this disclaimer to claims 1-4 and 9-21 of said patent.
*(Official Gazette, June 2, 1998)*